(12) United States Patent
Canich

(10) Patent No.: US 6,455,458 B1
(45) Date of Patent: Sep. 24, 2002

(54) TETHERED MONOCYCLOPENTADIENYL POLYMERIZATION CATALYSTS

(75) Inventor: Jo Ann M. Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/349,678

(22) Filed: Jul. 8, 1999

Related U.S. Application Data

(60) Provisional application No. 60/092,419, filed on Jul. 10, 1998.

(51) Int. Cl.$^7$ .............................. B01J 21/00; B01J 21/06
(52) U.S. Cl. ....................... 502/117; 502/113; 502/167; 556/11; 556/12; 556/28; 556/43
(58) Field of Search ................................. 502/113, 117, 502/167; 556/11, 12, 28, 43

(56) References Cited

U.S. PATENT DOCUMENTS

| | | | |
|---|---|---|---|
| 5,055,438 A | 10/1991 | Canich | 502/117 |
| 5,372,980 A | 12/1994 | Davis | 502/103 |
| 5,442,020 A | 8/1995 | Davis | 526/127 |
| 5,444,145 A | 8/1995 | Brant et al. | 526/348.3 |
| 5,585,508 A | 12/1996 | Küber et al. | 556/11 |
| 5,627,117 A | 5/1997 | Mukaiyama et al. | 502/113 |
| 5,693,730 A | 12/1997 | Küber et al. | 526/127 |
| 5,776,851 A | 7/1998 | Küber et al. | 502/103 |
| 5,869,586 A | 2/1999 | Riedel et al. | 526/170 |
| 5,880,302 A | 3/1999 | Herrmann et al. | 556/28 |
| 5,892,079 A | 4/1999 | Wilson, Jr. | 556/11 |
| 6,069,213 A * | 5/2000 | Nemzek et al. | 526/113 |
| 6,153,776 A | 11/2000 | Patton et al. | |

FOREIGN PATENT DOCUMENTS

| | | |
|---|---|---|
| CA | 2165927 | 6/1996 |
| CA | 2175159 | 10/1996 |
| CA | 2192770 | 6/1997 |
| EP | 0 664 304 A2 | 7/1995 |
| EP | 0 985 676 A1 | 3/2000 |
| WO | WO 92/00333 | 1/1992 |
| WO | WO 99/14222 | 3/1999 |
| WO | WO 99/20637 | 4/1999 |
| WO | WO 99/20665 | 4/1999 |

OTHER PUBLICATIONS

"$\mu$[1,1,2,2–Tetrakis($\eta^6$–phenyl)–1,2,–diphenyldisilane]–divanadium: Long Distance Exchange Interaction Mediated through a <SiPh–SiPh>Unit$^1$", Elschenbroich, et al, Inorg. Chem, vol. 32, pp. 5421–5424, (1993), No month.

"Monocyclopentadienyl–Type Titanium Complexes with the [$\eta^5\eta^5$–(C$_5$H$_4$)$_2$SlMe$_2$]$^{2-}$ Ligand. X–ray Crystal Structure of [(TiCl)$_2$($\mu_2$–O){$\mu_2$–$\eta$5–$\eta$5–(C$_5$H$_4$)$_2$SiMe$_2$}]$_2$($\mu_2$O)$_2$. The First Example of a Nonplanar "Ti$_4$O$_4$" Core", Ciruelos, et al, Organometallics, vol. 12, pp. 944–948, (1993), No month.

"Efficient Synthesis of rac–(Ethylenebis (indenyl) ZrX$_2$ Complexes via Amine Elimination", Diamond, et al. Organometallics, vol. 14, pp. 5–7, (1995) No month.

"Polymerizations of the ethylene and styrene initiated with trisiloxane–bridged dinuclear titanium metallocene/MMAO catalyst systems", Lee, et al, Macromol. Rapid Commun., vol. 16, pp. 265–268, (1995), no month.

"Synthesis of poly(tetrahyrofuran–b–ϵ–caprolactone) macromonomer via the SmI$_2$–induced transformation", Nomura, et al., Polymer Bulletin, vol. 35, pp. 683–689, (1995), No month.

"A series of Bi–and Mono–nuclear Ti(IV), Ti (III), and Ti(II) Complexes Containing the Dianion and Monoanion of Bis-(cyclopentadienyl) methane as Ligand", Stempfle, et al, Gazzetta Chimica, Italiana, vol. 125, pp. 287–289, (1995), No month.

"New evidence of the presence of internal electron donors in active sites of heterogenous Ziegler–Natta catalysts", Xu, et al, Macromol. Rapid Commun., vol. 17, pp. 645–651, (1996), No month.

"New mono–and bi–nuclear ansa–metallocenes of zirconium and hafnium as catalyts for the polymerisation of ethene and propene", Diamond, et al, J. Chem. Soc., Dalton Trans., pp. 921–938, (1996), No month.

"Polymerizations of Ethylene with Dinuclear Hexamethyltrisiloxanediylbis– (cyclopentadienylindenylzirconium dichloride)", Lee, et al, Korea Polymer Journal, vol. 4, No. 2, pp. 107–111, (1996), No month.

"Synthesis and catalytic properties of ansa–binuclear metallocenes of the Group IV transition metals", Ushioda, et al, Journal of Organometallic Chemistry, vol. 518, pp. 155–166, (1996), No. month.

(List continued on next page.)

Primary Examiner—Elizabeth Wood
(74) Attorney, Agent, or Firm—William G. Muller; Stephen D. Prodnuk; Charles E. Rumyan, Jr.

(57) ABSTRACT

The invention is a polymerization catalyst system derived from tethered, heteroatom-bridged monocyclopentadienyl transition metal compound precursor from Group 4 of the Periodic Table of the Elements. The catalyst system comprises an activated, tethered pair of Group 4 transition metal compounds having a bidentate ancillary ligand system consisting of one cyclopentadienyl group bound to the transition metal and a Group 15 or Group 16 atom covalently bound to the transition metal and linked to the cyclopentadienyl group through a bridging group containing a Group 14–15 element. The ligand systems of each transition metal compound are tethered by at least one tethering group comprising a Group 13–16 element connected at both ends to either the Group 15 or Group 16 atom or the Groups 14–15 bridging group element. The catalyst system can be employed to polymerize olefins to produce a high molecular weight polymer.

7 Claims, 4 Drawing Sheets

OTHER PUBLICATIONS

"Synthesis, characterization, and reactivities of the polysiloxane–bridged binuclear metallocenes tetramethyldisiloxanediylbis (cyclopentadienyltitanium trichloride) and hexamethyltrisiloxanediylbis ( cyclopentadienyltitanium trichloride)", Noh, et al, Journal of Organometallic Chemistry, vol. 518, pp. 1–6, (1996), No month.

"Synthesis, Structure, and Reactivity of rac–Me$_2$Si(indenyl)$_2$Zr(NMe$_2$)$_2$"Christopher, et al, Organometallics, vol. 15, pp. 4038–4044, (1996),No month.

"Synthesis of Group 4 Metal rac –(EBI)M (NR$_2$)$_2$ Complexes by Amine Elimination. Scope and Limitations" Diamond, et al, Organometallics, vol. 15, pp. 4030–4037, (1996), No month.

"New Examples of Half–Sandwich (Borylcyclopentadienyl)titanium Trichloride Complexes and an X–ray Structural Characterization of the Homobimetallic Complex [TiCl$_3$ {$\Theta^5$–C$_5$H$_4$}]$_2$BPh", Larkin, et al, Organometallics, vol. 15, pp. 2393–2398, (1996), No month.

"Efficient Synthesis of Chiral ansa–Metallocenes by Amine Elimination. Synthesis, Structure and Reactivity of rac–(E-BI)Zr(NMe$_2$)$_2$", Diamond, et al, J. Am. Chem. Soc., vol. 118, pp. 8024–8033, (1996), No month.

Abstract—EP 0 654 476 A1 1994, No month.

Abstract—EP 0 739 897 A1 1996, No month.

Abstract—EP 0 742 225 A1 1996, No month.

Abstract—EP 0 779 295 A1 1996, No month.

Abstract—EP 0 779 306 A2 1996, No month.

Abstract—DE 44 46 922 A1 1994, No month.

* cited by examiner

US 6,455,458 B1

TETHERED MONOCYCLOPENTADIENYL POLYMERIZATION CATALYSTS

RELATED APPLICATIONS

This application claims the benefit of U.S. Provisional Application No. 60/092,419 filed Jul. 10, 1998.

FIELD OF THE INVENTION

This invention relates to certain transition metal compounds from Group 4 of the Periodic Table of Elements, and to a catalyst system comprising a Group 4 transition metal compound and alumoxane, modified alumoxane, non-coordinating anion activator, Lewis acid, or the like to form an active catalyst species for the production of polyolefins such as polyethylene, polypropylene and alpha-olefin copolymers of ethylene and propylene having a high molecular weight.

BACKGROUND OF THE INVENTION

Monocyclopentadienyl heteroatom compounds are now well known as components for olefin polymerization catalysts. Bimetallic and polymetallic monocyclopentadienyl-bridged polymerization catalysts are also known. Monocyclopentadienyl transition metal complexes which are bridged to another monocyclopentadienyl transition metal complex are disclosed, for example, in Ciruelos et al., *Organometallics*, vol. 12, pp. 944–948 (1993); Lee et al., *Macromol. Rapid Commun.*, vol. 16, pp. 265–268 (1995); and Larkin et al., *Organometallics*, vol. 15, pp. 2393–2398 (1996). Ciruelos et al. also disclose direct bridging of the transition metal with an oxygen atom. Bridged monocyclopentadienyl transition metal complexes including heteroatom (amine) ligands are disclosed in Diamond et al., *Organometallics*, vol. 14, pp. 5–7 (1995); Diamond et al., *Organometallics*, vol. 15, pp. 4030–4037 (1996); Christopher et al., *Organometallics*, vol. 15, pp. 4038–4049 (1996); and Diamond et al., *J. Am. Chem. Soc.* vol. 118, pp. 8024–8033 (1996). However, none of these compounds contain bulky amine ligands.

Bis(cyclopentadienyl) transition metal complexes are bridged together via the cyclopentadienyl groups in bimetallic and polymetallic compounds described in, for example, Nomura et al., *Polymer Bulletin*, vol. 35, pp. 683–689 (1995); Stempfl et al., *Gazzetta Chimica Italiana*, vol. 125, pp. 287–290 (1995); Ushioda et al., *Journal of Organometallic Chemistry*, vol. 518, pp. 155–166 (1996); Lee et al., *Korea Polymer Journal*, vol. 4, pp. 107–111 (1996); Xu et al., *Macromol. Rapid Commun.*, vol. 17, pp. 645–651 (1996); Diamond et al., *J. Chem Soc., Dalton Trans.*, pp. 921–938 (1996); DE 4,446,922 (1996); EP 664,304; and U.S. Pat. No. 5,627,117 to Mukaiyama et al. U.S. Pat. Nos. 5,372,980 and 5,442,020, both to Davis, disclose bridged bis(cyclopentadienyl) transition metal complexes wherein the cyclopentadienyl groups in each complex are bridged together and two complexes are tethered together via the cyclopentadienyl groups and the bridging groups.

U.S. Pat. No. 5,444,145 to Brant et al., and U.S. Pat. No. 5,055,438 to Canich, and WO 92100333, disclose monocyclopentadienyl heteroatom transition metal complexes wherein the heteroatom is linked via a bridging group to the cyclopentadienyl group. The transition metal complexes can be bridged together directly via shared anionic ligands. Noh et al., *Journal of Organometallic Chemistry*, vol. 518, pp. 1–6 (1996) disclose polysiloxane-bridged binuclear and polynuclear monocyclopentadienyl transition metal compounds. U.S. Pat. No. 5,693,730 to Küber et al. discloses polynuclear metallocene compounds wherein bridged bis (cyclopentadienyl) transition metal complexes are tethered together via the cyclopentadienyl bridging group.

SUMMARY OF THE INVENTION

The catalyst system of this invention comprises a tethered pair of cyclopentadienyl transition metal compounds from Group 4 of the Periodic Table of the Elements, activated with an alumoxane, modified alumoxane, non-coordinating anion activator, Lewis acid or the like which may be employed in a solution, slurry, bulk or gas phase polymerization procedure to prepare a polyolefin. The metal compounds have a bidentate ancillary ligand system consisting of one cyclopentadienyl group covalently bound to the metal and a heteroatom group covalently bound to the transition metal, preferably linked to the cyclopentadienyl group by a bridging group containing a Group 14–15 element. The ligands are tethered by a tethering group containing a Group 13–16 element. The tethering group can be linked through the bridging groups, or a combination of the bridging groups and heteroatom groups, provided that when the tethering group is a hydrocarbylene diradical the bridging groups are independently di-alkyl, alkylenyl or diaryl silicon or germanium radical, when the tethering group is an oxygen diradical the bridging groups are free of silicon, and when the tethering groups contain silicon, germanium, nitrogen or phosphorus the bridging group is free of carbon. The tethering group can also be linked solely through the heteroatom groups.

A typical polymerization process according to the present invention, such as the polymerization or copolymerization of olefins, comprises the steps of contacting ethylene or $C_3$–$C_{20}$ alpha-olefins alone or with other unsaturated monomers including $C_3$–$C_{20}$ alpha-olefins, $C_4$–$C_{20}$ diolefins, and/or acetylenically unsaturated monomers) either alone or in combination with other olefins and/or other unsaturated monomers, with a catalyst comprising, in a suitable polymerization diluent, the tethered monocyclopentadienyl Group 4 transition metal component of the invention; and an alumoxane, modified alumoxane, non-coordinating anion activator, Lewis acid or the like, or combinations, in an amount to provide a molar aluminum, non-coordinating anion, or Lewis acid to transition metal ratio of from about 1:1 to about 20,000:1 or more; and reacting such monomer in the presence of such catalyst system at a temperature from about −100° C. to about 300° C. for a time from about one second to about 10 hours to produce a polyolefin having a weight average molecular weight of from about 1000 or less to about 5,000,000 or more, and a molecular weight distribution of from about 1.5 to about 15.0 or greater.

DETAILED DESCRIPTION OF THE INVENTION

Figure 1:
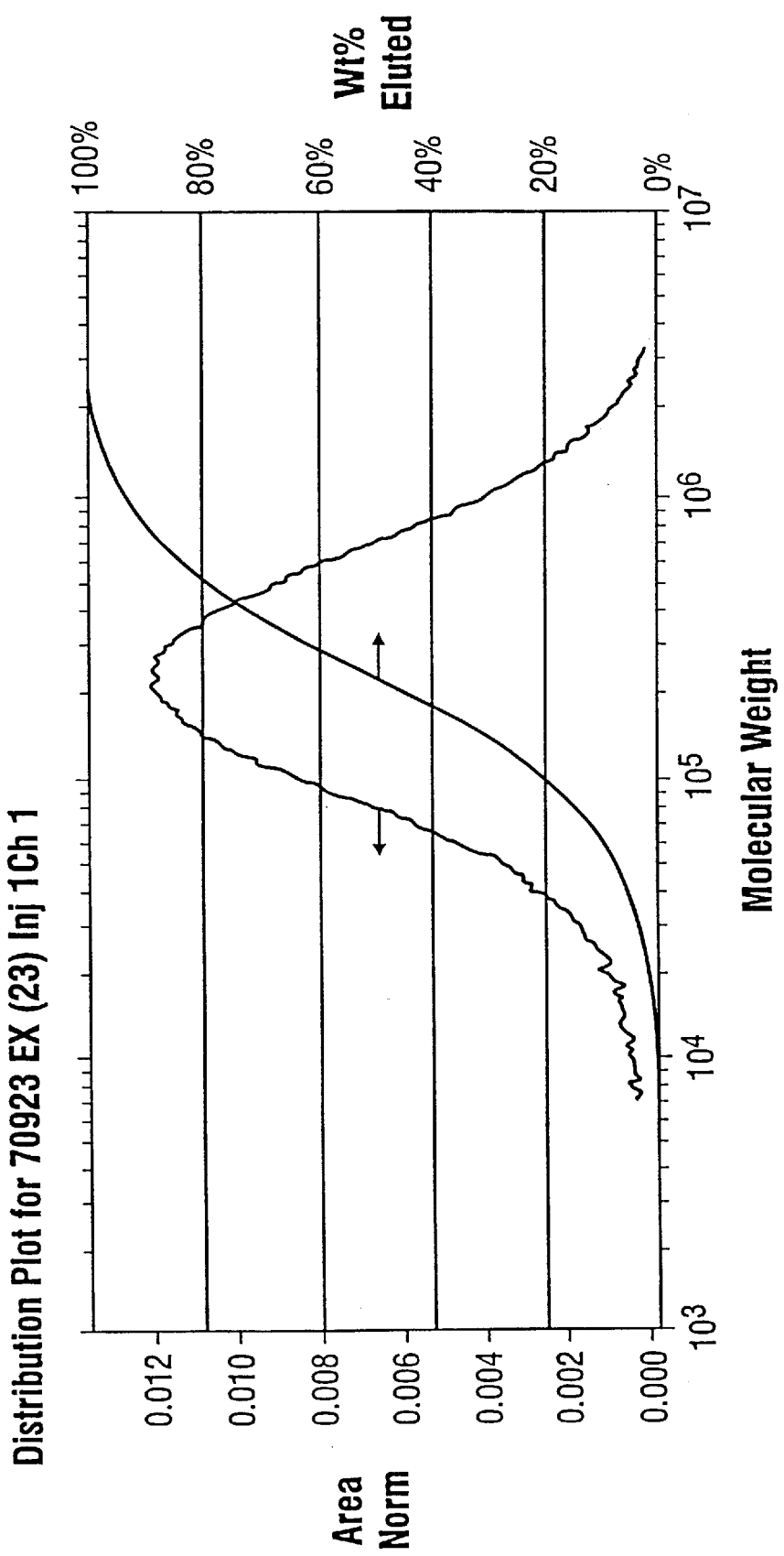
FIG. 1 is graph showing the molecular weight distribution of a polymer produced using the catalysts of the present invention.
Figure 2:
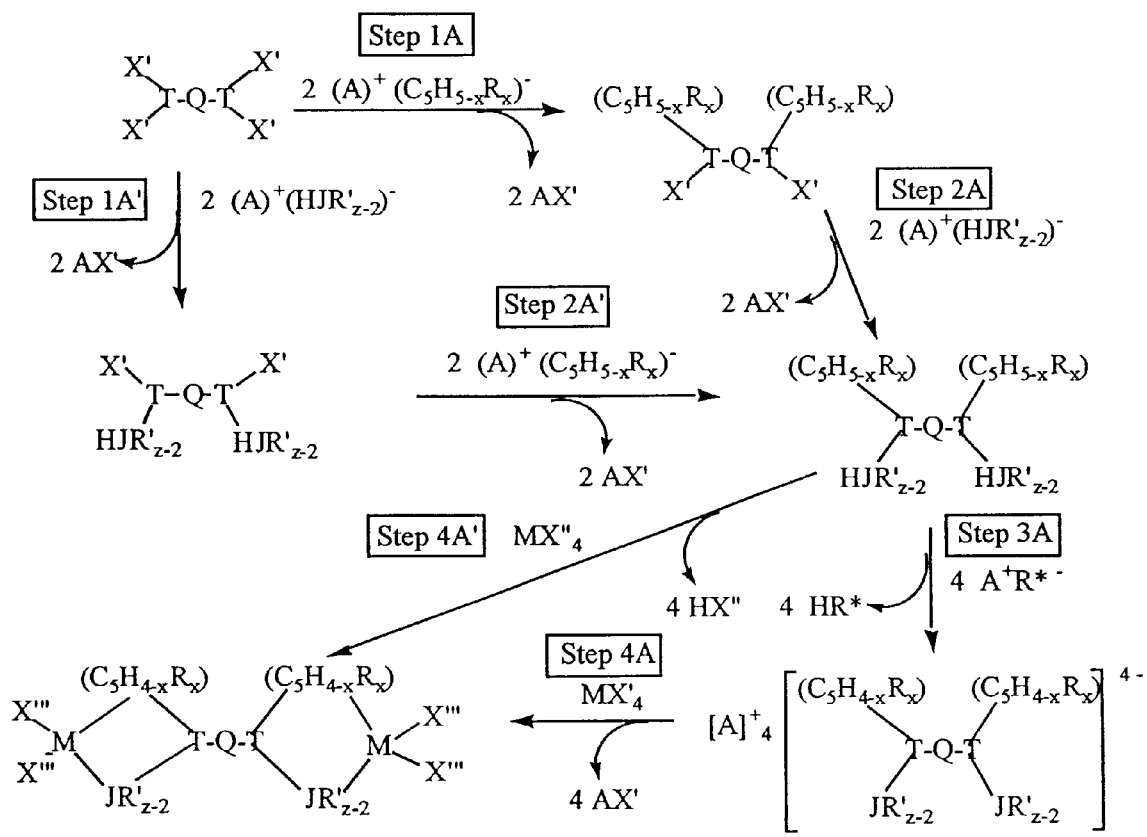
FIG. 2 shows a synthetic route to produce compounds of formula "A" as defined herein.
Figure 3:
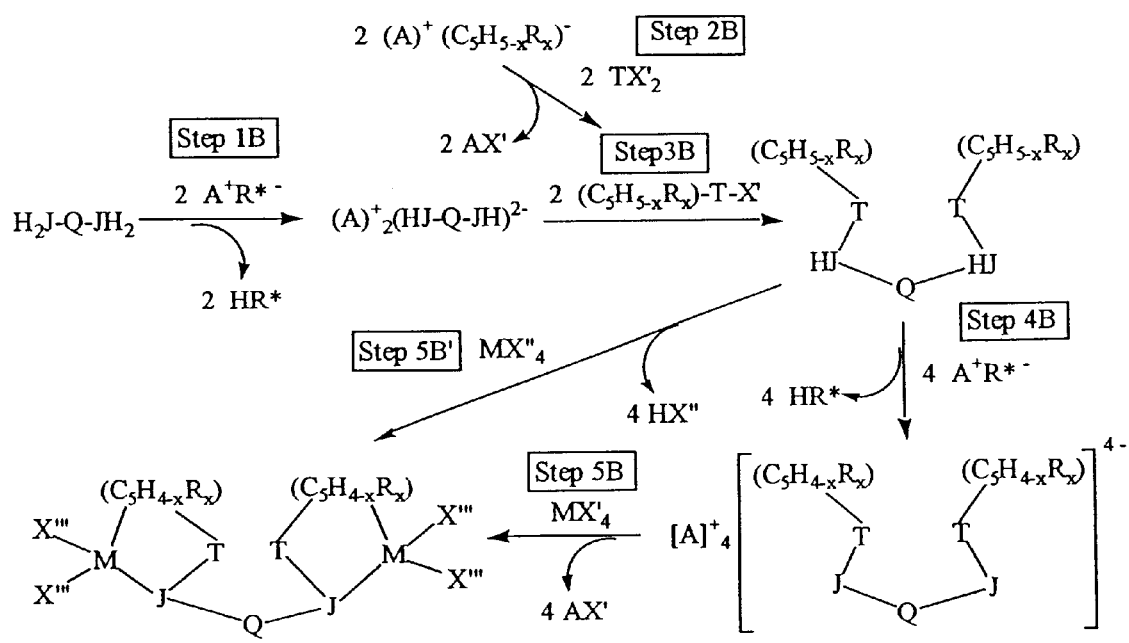
FIG. 3 shows a synthetic route to produce compounds of formula "B" (y=1) as defined herein.
Figure 4:
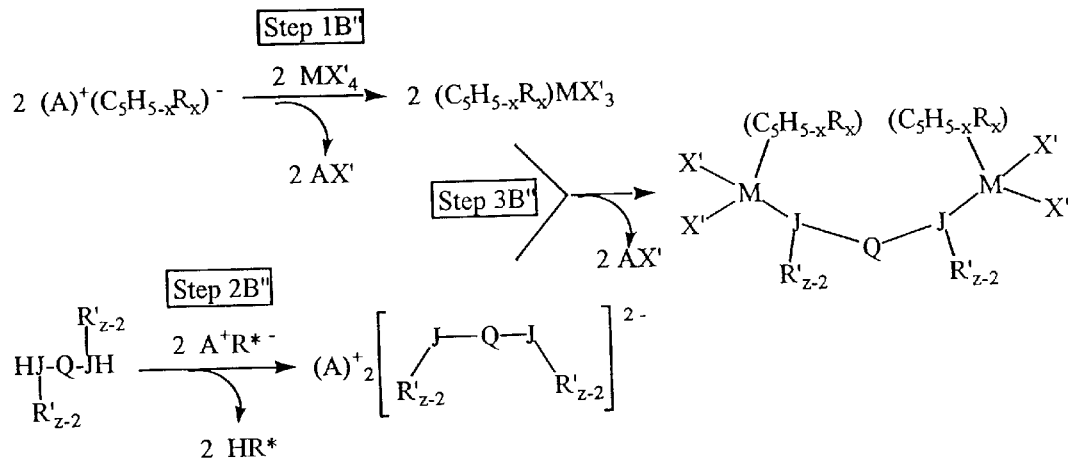
FIG. 4 shows a synthetic route to produce compounds of formula "B" (y=0) as defined herein.
Figure 5:
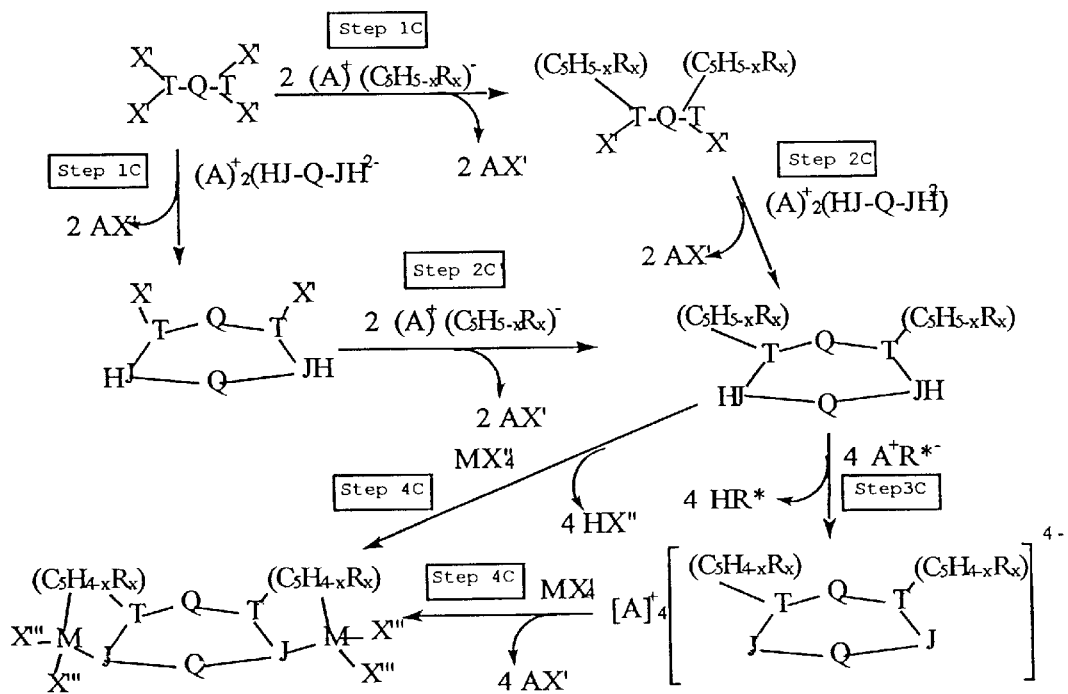
FIG. 5 shows a synthetic route to produce compounds of formula "C" as defined herein.

The Group 4 transition metal component of the catalyst system can be represented by one of the general formulae:

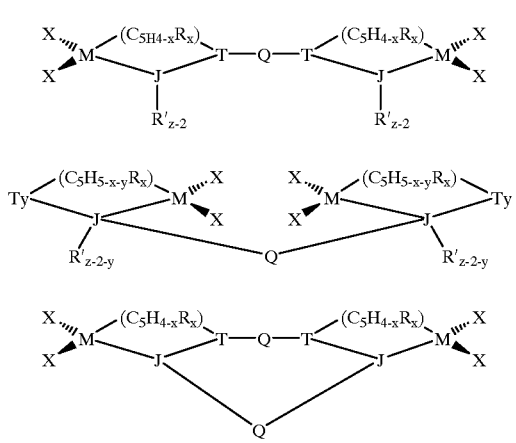

wherein

M is Ti, Zr or Hf;

each $C_5H_{5-x-y}R_x$, and $C_5H_{4-x}R_x$ are independently cyclopentadienyl rings substituted with from zero to four (in $C_5H_{4-x}R_x$) or five (in $C_5H_{5-x-y}R_x$), substituent groups R, x is a number from 0 to 4 (in $C_5H_{4-x}R_x$) or 5 (in $C_5H_{5-x-y}$), denoting the degree of substitution, and each substituent group R is, independently, a radical selected from the group consisting of $C_1$–$C_{20}$ hydrocarbyl radicals, substituted $C_1$–$C_{20}$ hydrocarbyl radicals wherein one or more hydrogen atoms is replaced by a halogen atom, $C_1$–$C_{20}$ hydrocarbyl-substituted metalloid radicals wherein the metalloid is selected from Group 14 of the Periodic Table of the Elements, and halogen radicals, or $C_5H_{5-x-y}R_x$, or $C_5H_{4-x}R_x$ is a cyclopentadienyl ring in which two adjacent R groups are joined forming a $C_4$–$C_{20}$ ring to give a saturated or unsaturated polycyclic cyclopentadienyl ligand such as indenyl, tetrahydroindenyl, fluorenyl or octahydrofluorenyl, or substituted indenyl or fluorenyl where a ring hydrogen is replaced with any $R_x$ as defined above;

each J is independently an element with a coordination number of three from Group 15 (in formulae A through C), or with a coordination number of two from Group 16 (in formulae A and B) of the Periodic Table of the Elements, preferably nitrogen, phosphorus, oxygen or sulfur;

each R' is, independently, a radical selected from the group consisting of $C_1$–$C_{20}$ hydrocarbyl radicals, substituted $C_1$–$C_{20}$ hydrocarbyl radicals wherein one or more hydrogen atoms is replaced by a halogen atom and $C_1$–$C_{20}$ hydrocarbyl-substituted metalloid radicals wherein the metalloid is selected from Group 14 of the Periodic Table of the Elements;

z is the coordination number of the element J (2 or 3);

each y is independently 0 or 1 denoting the optional presence of the bridging group T, provided that when y is 0 in formula (B), at least one R' preferably has three or more carbon atoms, e.g. a $C_3$–$C_{20}$ hydrocarbyl radical, a substituted $C_3$–$C_{20}$ hydrocarbyl wherein one or more hydrogen atoms is replaced by a halogen atom, or $C_3$–$C_{20}$ hydrocarbyl-substituted metalloid wherein the metalloid is selected from Group 14 of the Periodic Table of the Elements;

each T, when present, is independently a covalent bridging group containing a Group 14 or 15 element such as, but not limited to, a dialkyl, alkylaryl or diaryl silicon or germanium radical, alkyl or aryl phosphine or amine radical, or a hydrocarbyl radical such as methylene, ethylene, isopropylene or the like;

each X is independently a univalent anionic ligand such as halogen, hydride or substituted or unsubstituted $C_1$–$C_{20}$ hydrocarbyl, hydrocarbylsilyl, alkoxide, aryloxide, amide, or phosphide, provided that when any X is a hydrocarbyl such X is different from $C_5H_{5-x-y}R_x$, or $C_5H_{4-x}R_x$ or both X together may be an alkylidene, a cyclometallated hydrocarbyl or any other divalent anionic chelating ligand, or both X together may be a $C_4$–$C_{20}$ neutral diene ligand;

each Q is independently a diradical tethering group containing a Group 13–16 element, preferably a hydrocarbylene linkage such as a substituted alkylene, cycloalkylene or arylene diradical, or any combination thereof wherein such diradical is optionally substituted with a halide or a metalloid radical wherein the metalloid is selected from Group 14 of the Periodic Table of Elements, substituted silylene diradicals including those of formula $R''_2Si)_n$, siloxene diradicals including those of formula $R''_2Si(OSiR''_2)_n$, silazene diradicals including those of formula $R''_2C_2Si(NR''SiR''_2)_n$ and any combinations thereof such as hydrocarbylsilylene diradicals including those of formulas $R''_2Si(CR''_2)_n$, $R''_2C(SiR''_2)_nCR''_2$ and $R''_2Si(CR''_2)_nSiR''_2$, hydrocarbylsiloxene diradicals including those of formulas $R''_2Si(OSiR''_2)_nCR''_2$, $R''_2CR''_2Si(OSiR''_2)_nCR''_2$ and $R''_2Si(OSiR''_2)_nCR''_2SiR''_2(OSiR''_2)_n$ and hydrocarbylsilazene diradicals including those of formulas $R''_2SiR''N(CR''_2)_nNRSiR''_2$ and $R''SiN((CR''_2)_n)_2NSiR''$ where n is from 1 to 30 and R" is independently a hydrogen radical, a hydrocarbyl radical or a substituted hydrocarbyl radical including halocarbyl and hydrohalocarbyl radicals and any $CR''_2$ may independently be replaced by an aromatic diradical such as $C_6W''_4$, or an alicyclic diradical of formula $C_{n'}R''_{2n'-2}$ where n' is from 4 to 20 and R" is as previously defined. Q may also be a substituted Group 13 or 15 diradical such as BR', NR' or PR' where R' is as previously defined, or a Group 16 diradical such as O or S. In its simplest form, Q can be a simple bond between two T or J ligands or any combination thereof. Additionally, in any of the formulae above, one or more silicon atoms (Si) may be replaced by a germanium atom (Ge). For Q bonded to two T, Q is preferably from about 1 to 30 atoms bonded in series between the pair of cyclopentadienyl transition metal compounds, more preferably from about 1 to 20 atoms bonded in series between the pair of cyclopentadienyl transition metal compounds, and most preferably from about 1 to 10 atoms bonded in series between the pair of cyclopentadienyl transition metal compounds. For Q bonded to two J ligands, Q is preferably from about 2 to 40 atoms bonded in series more preferably from about 3 to 30 atoms bonded in series and most preferably from about 4 to 20 atoms bonded in series. An example of a Q diradical with two atoms bonded in series is $CH_2CH_2$; an example of a Q diradical with three atoms bonded in series is $Si(Me)_2OSi(Me)_2$, with the provisos that when Q is a hydrocarbylene diradical in =T=QT= in formula A or C, each T independently comprises a dialkyl, alkylaryl or diaryl silicon or germanium radical; when Q is an oxygen diradical in =T—Q—T= in formula A or C, each T does not contain silicon; and when Q in =T—Q—T= in formula A or C contains a Group 14 element other than carbon or a Group 15 element, such as silicon, germanium, nitrogen or phosphorus, each T does not contain carbon.

Exemplary diradicals for Q include linear or branched hydrocarbyl diradicals such as methylene (i.e. $CH_2$) and isomers of ethylene, propylene, butylene, pentylene, hexylene, heptylene, octylene, nonylene, decylene, undecylene, dodecylene, cyclobutylene, cyclohexylene, cycloheptylene, cyclooctylene, cyclodecylene, cyclododecylene, methylcyclohexylene, dimethylcyclohexylene, phenylene (i.e. $C_6H_4$), tolylene, xylylene and the like. Suitable silylene diradicals include dimethylsilylene (i.e. $SiMe_2$), diethylsilylene, di-n-propylsilylene, diisopropylsilylene, di-n-butylsilylene, di-n-hexylsilylene, methylphenylsilylene, diphenylsilylene, dicyclohexylsilylene, methylcyclohexylsilylene, tetramethyldisilylene (i.e. $SiMe_2SiMe_2$), 1,2-dimethyl-1,2-diphenyldisilylene, tetraphenyldisilylene, hexamethyltrisilylene (i.e. $SiMe_2SiMe_2SiMe_2$), 1,2,3-trimethyl-1,2,3-triphenyltrisilylene, octanethyltetrasilylene and the like. Suitable siloxene diradicals include tetramethyldisiloxene (i.e. $SiMe_2OSiMe_2$), tetraphenyldisiloxene, 1,3-dimethyl-1,3-diphenyldisiloxene, hexamethyltrisiloxene (i.e. $SiMe_2OSiMe_2OSiMe_2$), hexaphenyltrisiloxene, 1,3,5-trimethyl-1,3,5-triphenyltrisiloxene, octamethyltetrasiloxene, decamethylpentasiloxene, dodecamethylhexasiloxene and the like. Suitable silazene diradicals include 1,1,3,3-tetramethyldisilazene (i.e. $SiMe_2NHSiMe_2$), pentamethyldisilazene (i.e. $SiMe_2NMeSiMe_2$), 2-phenyl-1,1,3,3-tetramethyldisilazene, 1,1,3,3-tetraphenyldisilazene, pentaphenyldisilazene, 1,3-dimethyl-1,3-diphenyldisilazene, 1,1,3,3,5,5-hexamethyltrisilazene (i.e. $SiMe_2NHSiMe_2NHSiMe_2$), 2,4-diphenyl-1,1,3,3,5,5-hexamethyltrisilazene, octamethyltrisilazene (i.e. $SiMe_2NMeSiMe_2NMeSiMe_2$), 1,1,3,3,5,5-hexaphenyltrisilazene, octaphenyltrisilazene, 1,3,5-trimethyl-1,3,5-triphenyltrisilazene, 1,1,3,3,5,5,7,7-octamethyltetrasilazene, undecamethyltetrasilazene, 1,1,3,3,5,5,7,7,9,9-decamethylpentasilazene, tetradecamethylpentasilazene, 1,1,3,3,5,5,7,7,9,9,11,11-dodecamethylhexasilazene, heptadecamethylpentasilazene and the like. Suitable hydrocarbylsilylene diradicals include bis(1,1-methylene)dimethylsilane (i.e. $CH_2SiMe_2CH_2$), bis(1,1-phenylene)dimethylsilane, bis(1,1-methylene)diphenylsilane, bis(1,1-methylene)methylphenylsilane, bis(1,2-methylene)tetramethyldisilane (i.e. $CH_2SiMe_2SiMe_2CH_2$), bis(1,2-phenylene)tetramethyldisilane, bis(1,3-methylene)hexamethyltrisilane, bis(1,4-methylene)octamethyltetrasilane, 1,1-bis(dimethylsilylene)methane (i.e. $SiMe_2CH_2SiMe_2$), 1,2-bis(dimethylsilylene)ethane (i.e. $SiMe_2CH_2CH_2SiMe_2$), 1,3-bis(dimethylsilylene)propane, 1,4-bis(dimethylsilylene)butane, 1,6-bis(dimethylsilylene)hexane, 1,8-bis(dimethylsilylene)octane, 1,1-bis(diphenylsilylene)methane, 1,2-bis(diphenylsilylene)ethane, 1,3-bis(diphenylsilylene)propane, 1,4-bis(diphenylsilylene)butane, 1,6-bis(diphenylsilylene)hexane, 1,8-bis(diphenylsilylene)octane, o-, m- or p-bis(dimethylsilylene)benzene, bis[(2-dimethylsilylene)ethyl]benzene (i.e. $SiMe_2CH_2CH_2C_6H_4CH_2CH_2SiMe_2$), bis[(1-dimethylsilylene)methyl]benzene, o-, m- or p-bis(diphenylsilylene)benzene, bis[(2-diphenylsilylene)ethyl]benzene, bis[(1-diphenylsilylene)methyl]benzene, 1,1-bis(tetramethyldisilylene)methane (i.e. $SiMe_2SiMe_2CH_2SiMe_2SiMe_2$), 1,2-bis(tetramethyldisilylene)ethane (i.e. $SiMe_2SiMe_2CH_2CH_2SiMe_2SiMe_2$), 1,3-bis(tetramethyldisilylene)propane, 1,4-bis(tetramethyldisilylene)butane, 1,6-bis(tetramethyldisilylene)hexane, 1,1-bis(tetraphenyldisilylene)methane, 1,2-bis(tetraphenyldisilylene)ethane, 1,3-bis(tetraphenyldisilylene)propane, 1,4-bis(tetraphenyldisilylene)butane, 1,6-bis(tetraphenyldisilylene)hexane, o-, m- or p-bis(tetramethyldisilylene)benzene, 1,1-bis(hexamethyltrisilylene)methane (i.e. $SiMe_2SiMe_2SiMe_2CH_2SiMe_2SiMe_2SiMe_2$), 1,2-bis(hexamethyltrisilylene)ethane (i.e. $SiMe_2SiMe_2SiMe_2CH_2CH_2SiMe_2SiMe_2SiMe_2$), 1,3-bis(hexamethyltrisilylene)propane, 1,4-bis(hexamethyltrisilylene)butane, 1,6-bis(hexamethyltrisilylene)hexane, 1,1-bis(hexamethyltrisilylene)methane, 1,2-bis(hexamethyltrisilylene)ethane, 1,3-bis(hexamethyltrisilylene)propane, 1,4-bis(hexamethyltrisilylene)butane, 1,6-bis(hexamethyltrisilylene)hexane, 1-, m- or p-bis(hexamethyltrisilylene)benzene, dimethylsilaethylene (i.e. $SiMe_2CH_2$), diphenylsilaethylene, methylphenylsilaethylene, dimethylsilapropylene, diphenylsilapropylene, methylphenylsilapropylene, α,α-dimethylsilabenzylene (i.e. $SiMe_2C_6H_4$), α,α-diphenylsilabenzylene, α,α-methylpbenylsilabenzylene, tetraiethyldisilapropylene (i.e. $SiMe_2SiMe_2CH_2$), tetramethyldisilabutylene, hexamethyltrisilabutylene, hexamethyltrisilapentylene, octahethyltetrasilapentylene, octamethyltetrasilahexylene, and the like. Suitable hydrocarbylsiloxene diradicals include bis(1,3-methylene)-1,1,3,3-tetramethyldisiloxane (i.e. $CH_2SiMe_2OSiMe_2CH_2$), bis(1,3-ethylene)-1,1,3,3-tetramethyldisiloxane, bis(1,3-phenylene)-1,1,3,3-tetramethyldisiloxane, bis(1,5-methylene)-1,1,3,3,5,5-hexarnethyltrisiloxane, bis(1,5-ethylene)-1,1,3,3,5,5-hexamethyltrisiloxane, bis(1,5-phenylene)-1,1,3,3,5,5-hexamethyltrisiloxane, bis(1,7-methylene)-1,1,3,3,5,5,7,7-octamethyltetrasiloxane, bis(1,7-ethylene)-1,1,3,3,5,5,7,7-octamethyltetrasiloxane, bis(1,7-phenylene)-1,1,3,3,5,5,7,7-octamethyltetrasiloxane, 1,1-bis(tetramethyldisiloxene)methane (i.e. $SiMe_2OSiMe_2CH_2SiMe_2OSiMe_2$), 1,2-bis(tetramethyldisiloxene)ethane, 1,3-bis(tetramethyldisiloxene)propane, 1,4-bis(tetramethyldisiloxene)butane, 1,6-bis(tetramethyldisiloxene)hexane, 1,8-bis(tetramethyldisiloxene)octane, 1,1-bis(tetraphenyldisiloxene)methane, 1,2-bis(tetraphenyldisiloxene)ethane, 1,3-bis(tetraphenyldisiloxene)propane, 1,4-bis(tetraphenyldisiloxene)butane, 1,6-bis(tetraphenyldisiloxene)hexane, 1,8-bis(tetraphenyldisiloxene)octane, o-, m- or p-bis(tetramethyldisiloxene)benzene, bis[(2-tetramethyldisiloxene)ethyl]benzene (i.e. $SiMe_2OSiMe_2CH_2CH_2C_6H_4CH_2CH_2SiMe_2OSiMe_2$), bis[(1-tetramethyldisiloxene)methyl]benzene, o-, m- or p-bis(tetraphenyldisiloxene)benzene, bis[(2-tetraphenyldisiloxene)]ethylbenzene, bis[(1-tetraphenyldisiloxene)methyl]benzene, 1,1-bis(hexamethyltrisiloxene)methane (i.e. $SiMe_2OSiMe_2OSiMe_2CH_2SiMe_2OSiMe_2OSiMe_2$), 1,2-bis(hexamethyltrisiloxene)ethane, 1,3-bis(hexamethyltrisiloxene)propane, 1,4-bis(hexamethyltrisiloxene)butane, 1,6-bis(hexamethyltrisiloxene)hexane, 1,1-bis(hexaphenyltrisiloxene)methane, 1,2-bis (hexaphenyltisiloxene)ethane, 1,3-bis (hexaphenyltrisiloxene)propane, 1,4-bis (hexaphenyltrisiloxene)butane, 1,6-bis (hexaphenyltrisiloxene)hexane, o-, m- or p-bis (hexamethyltrisiloxene)benzene, (tetramethyldisiloxyl) methylene (i.e. $SiMe_2OSiMe_2CH_2$), (tetraphenyldisiloxyl) methylene, (tetramethyldisiloxyl)ethylene, (tetraphenyldisiloxyl)ethylene, (tetramethyldisiloxyl) phenylene (i.e. $SiMe_2OSiMe_2C_6H_4$), (tetraphenyldisiloxyl) phenylene, (hexamethyltrisiloxyl)methylene, (hexamethyltrisiloxyl)ethylene, (hexamethyltisiloxyl) phenylene, (octamethyltetrasiloxyl)methylene, (octamethyltetrasiloxyl)ethylene, (octamethyltetrasiloxyl) phenylene and the like. Suitable hydrocarbylsilazene diradicals include N,N'-bis(dimethylsilylene)piperazine, N,N'-bis(diphenylsilylene)piperazine, N,N'-bis(dimethylsilylene) pyrazine, N,N'-bis(diphenylsilylene)pyrazine, N,N'-bis(dimethylsilylene)pyridazine, N,N'-bis(diphenylsilylene) pyridazine, N,N'-bis(dimethylsilylene)pyrimidine, N,N'-bis(diphenylsilylene)pyrimidine, bis(trimethylsilazene) methane (i.e. $SiMe_2NMeCH_2NMeSiMe_2$), bis(1,1-dimethyl-2-phenylsilazene)methane, bis(1,1-diphenyl-2-methylsilazene)methane, bis(triphenylsilazene)methane, 1,2-bis(trimethylsilazene)ethane (i.e. $SiMe_2NMeCH_2CH_2NMeSiMe_2$), 1,2-bis(1,1-dimethyl-2-phenylsilazene)ethane, 1,2-bis(1,1-diphenyl-2-methylsilazene)ethane, 1,2-bis(triphenylsilazene)ethane, o-, m- or p-bis(trimethylsilazene)benzene, o-, m- or p-bis(1,1-dimethyl-2-phenylsilazene)benzene, o-, m- or p-bis(1,1-diphenyl-2-methylsilazene)benzene, o-, m- or p-bis (triphenylsilazene)benzene, 1,6-bis(trimethylsilazene) hexane, 1,6bis(1,1-dimethyl-2-phenylsilazene)hexane, 1,6-bis(1,1-diphenyl-2-methylsilazene)hexane, 1,6-bis (triphenylsilazene)hexane, and the like. Other suitable Q diradicals include dimethylgermylene (i.e. $GeMe_2$), diphenylgermylene, tetramethyldigeimylene (i.e. $GeMe_2GeMe_2$), tetraphenyldigermylene, dimethylsilyldimethylgermyl (i.e. $SiMe_2GeMe_2$), dimethylsilyldiphenylgermyl, diphenylsilyldimethylgermyl, diphenylsilyldiphenylgermyl, diphenylgermaethylene (i.e. $GePh_2CH_2$), dimethylgermaethylene and the like.

Suitable hydrocarbyl and substituted hydrocarbyl radicals, which may be substituted as an R group for at least one hydrogen atom in the cyclopentadienyl ring, will contain from 1 to about 20 carbon atoms and include straight and branched alkyl radicals, cyclic hydrocarbon radicals, alkyl-substituted cyclic hydrocarbon radicals, aromatic radicals, alkyl-substituted aromatic radicals and cyclopentadienyl rings containing one or more fused saturated or unsaturated rings. Suitable organometallic radicals, which may be substituted as an R group for at least one hydrogen atom in the cyclopentadienyl ring, include trimethylsilyl, triethylsilyl, ethyldimethylsilyl, methyldiethylsilyl, triphenylgermyl and the like. Examples of cyclopentadiene ring groups ($C_5H_{5-x-y}R_x$, or $C_5H_{4-x}R_x$) which are suitable as a constituent group of the transition metal component of the catalyst system are identified in column 2 of Table 1 under the heading ($C_5H_{5-x-y}R_x$ or ($C_5H_{4-x}R_x$).

Suitable hydrocarbyl and substituted hydrocarbyl radicals, which may be substituted as an R' group for at least one hydrogen atom in the heteroatom J ligand group, will contain from one to about 20 carbon atoms and include straight and branched alkyl radicals, cyclic hydrocarbon radicals, alkyl substituted cyclic hydrocarbon radicals, aromatic radicals and alkyl-substituted aromatic radicals and organometalloid substituted alkyl, cycloalkyl and aromatic radicals. When y=0 in Formula B, R' is preferably from 3 to about 20 carbon atoms and at least one R' is preferably a bulky hydrocarbyl or substituted hydrocarbyl radical bonded to J through a 2°, 3° or aromatic carbon atom. Examples of heteroatom ligand groups (R') which are suitable as a constituent group of the Group 4 transition metal component of the catalyst system are identified in column 3 of Table 1 under the heading $Jz_{-2}$, $JR'z_{-2-y}$ or J.

Exemplary hydrocarbyl radicals for the X are methyl, ethyl, propyl, butyl, amyl, isoamyl, hexyl, isobutyl, heptyl, octyl, nonyl, decyl, cetyl, 2-ethylbexyl, phenyl and the like, with methyl being preferred. Exemplary halogen atoms for X include chlorine, bromine, fluorine and iodine, with chlorine being preferred. Exemplary alkoxides and aryloxides for X are methoxide, phenoxide and substituted phenoxides such as 4-methylphenoxide. Exemplary amides for X are dimethylamide, diethylamide, methylethylamide, di-t-butylamide, diisopropylamide and the like. Exemplary arylamides are diphenylamide and any other substituted phenylamides. Exemplary phosphides for X are diphenylphosphide, dicyclohexylphosphide, diethylphosphide, dimethylphosphide and the like. Exemplary alkylidene radicals for both X together are methylidene, ethylidene and propyledine. Exemplary cyclometallated hydrocarbyl radicals for both X together are propylene, and isomers of butylene, pentalene, hexalene and octylene. Exemplary dienes for both X together are 1,3-butadiene, 1,3-pentadiene, 1,4-pentadiene, 1,3-hexadiene, 1,4-hexadiene, 1,5-hexadiene, 2,4-dimethyl-1,3-butadiene, 2-methyl-1,3-pentadiene, 2-methyl-1,3-hexadiene and 2,4-hexadiene. Examples of the X group which are suitable as a constituent group or element of the group for transition metal component of the catalyst system are identified in column 4 of Table 1 under the heading "X".

Table 1 depicts representative constituent moieties for the Group 4 transition metal components of the present catalyst system, but the list is for illustrative purposes only and should not be construed to be limiting in any way. A number of final components may be formed by permuting all possible combinations of the constituent moieties with each other. Some changes in nomenclature may be required. Illustrative compounds tethered through the T ligand are bis[dichlorohafnium {(tetramethylcyclopentadienyl)(t-butylamido)methylsilanetriyl}]hexylene; bis [dichlorozirconium {(3-methylcyclopentadienyl)(phenylamido)phenylsilanetriyl}]dodecylene; and bis [dimethyltitanium {(tetramethylcyclopentadienyl)(phenylamido)phenylsilanetriyl}]octylene. Illustrative compounds tethered through the J ligand are bis [dichlorotitanium {(tetramethylcyclopentadienyl)(amido)dimethylsilylene]dodecylene; bis-m-[dichlorozirconium (pentamethylcyclopentadienyl)(methylamido)]phenylene; and bis[dichlorohafnium (cyclopentadienyl)(n-butylamido)]octylene.

TABLE 1

| T | (C₅H₅₋ₓ₋ᵧRₓ), or (C₅H₄₋ₓRₓ) | (JU'_{z-2}), (JR'_{z-2-y}), or J | X | M | Q* |
|---|---|---|---|---|---|
| (y = 1; formula B) | (x = 0) | (formulae A, B (y = 0), | | | |
| Dimethylsilylene | Cyclopentadienyl | Methylamido | hydride | titanium | Methylene |
| Diethylsilylene | | Ethylamido | chloro | zirconium | Ethylene |
| di-n-propylsilylene | (x = 1) | n-propylamido | fluoro | hafnium | Propylene |
| Diisopropylsilylene | Methylcyclopentadienyl | Isopropylamido | bromo | | Butylene |
| di-n-butylsilylene | Ethylcyclopentadienyl | n-butylamido | iodo | | Hexylene |
| di-t-butylsilylene | n-propylcyclopentadiene | i-butylamido | methyl | | Octylene |
| di-n-hexylsilylene | i-propylcyclopentadienyl | t-butylamido | Ethyl | | Dodecylene |
| Methylphenylsilylene | n-butylcyclopentadienyl | n-hexylamido | n-propyl | | Cyclohexylene |
| Ethylmethylsilylene | t-butylcyclopentadienyl | n-octylamido | Isopropyl | | Cyclooctylene |
| Diphenylsilylene | (cyclohexylmethyl)cyclopentadienyl | Phenylamido | N-butyl | | Cyclododecylene |
| di(p-t-butylphenethyl)silylene | n-hexylcyclopentadienyl | P-n-butylphenylamido | Isobutyl | | Phenylene |
| n-hexylmethylsilylene | n-octylcyclopentadienyl | 2,5-di-t-butylphenylamido | Amyl | | Xylylene |
| Cyclopentamethylenesilylene | β-phenylpropylcyclopentadienyl | Perfluorophenylamido | Isoamyl | | Dimethylsilylene |
| Cyclotetramethylenesilylene | Phenylcyclopentadienyl | Benzylamido | Hexyl | | Diethylsilylene |
| Dimethylgermylene | Benzylcyclopentadienyl | Cyclohexylamido | Heptyl | | di-n-propyl-silylene |
| Diphenylgermylene | (diphenylmethylcyclopentadienyl | Cyclooctylamido | Octyl | | Diisopropyl-silylene |
| Methylene | Trimethylgermylcyclopentadienyl | Cyclodecylamido | Nonyl | | di-n-butylsilylene |
| Dimethylmethylene | Trimethylstannylcyclopentadienyl | Cyclododecylamido | Decyl | | di-n-hexylsilylene |
| Diphenylmethylene | Thriethylplumylcyclopentadienyl | 2-norbornylamido | Cetyl | | Methylphenyl-silylene |
| Ethylene | Trifluoromethylcyclopentadienyl | 1-adamantylamido | Phenyl | | Diphenylsilylene |
| 1,1,2,2-tetramethylethylene | Trimethylsilylcyclopentadienyl | Ethylphosphido | Benzyl | | Dicyclohexyl-silylene |
| 1,1-dimethylethylene | | Phenylphosphido | (trimethylsilyl)methyl | | Tetramethyl-disilylene |
| 1,2-dimethylethylene | (x = 2) | Cyclohexylphosphido | Methoxy | | Tetraphenyl-disilylene |
| 1,2-dipropylethylene | 1,2-dimethylcyclopentadienyl | Oxo | Ethoxy | | Hexamethyl-trisilylene |
| Propylene | 1,3-dimethylcyclopentadienyl | Sulfido | Propoxy | | Octamethyl-tetrasilylene |
| 1,1,3,3-tetramethylpropylene | 1,2-diethylcyclopentadienyl | | Butoxy | | Tetramethyl-disiloxene |
| 1,1,3,3-tetraethylpropylene | 1,3-diethylcyclopentadienyl | | Phenoxy | | Hexamethyl-trisiloxene |
| 1,3-dimethylpropylene | 1,3-di-n-propylcyclopentadienyl | | Dimethylamido | | Pentamethyl-disilazene |
| 1,3-diethylpropylene | 1,3-diphenylcyclopentadienyl | | diethylamido | | Octamethyl-trisilazene |
| 1,1-dimethyl-3,3-diethyl-propylene | 1,2-diphenylcyclopentadienyl | | Methylethylamido | | Bis(1,1-methylene)dimethylsilane |
| Tetramethyldisiloxene | 1-methyl-3-phenylcyclopentadienyl | | Di-t-butylamido | | 1,1-bis(dimethyl-silylene)methane |
| 1,2-bis(dimethylsilylene)ethane | 1-methyl-3-t-butylcyclopentadienyl | | Diphenylamido | | 1,1,4,4-tetra-methyldisila-propylene |
| Methylazanediyl | 1-methyl-3-isopropylcyclopentadienyl | | Diphenylphosphido | | (tetramethyl-disiloxyl)ethylene |
| Phenylazanediyl | 1-methyl-3-n-butylcyclopentadienyl | | Dicyclohexyl-phosphido | | N,N'-bis(di-methylsilylene)pyrazine |
| t-butylazanediyl | 1-cyclohexyl-3-methylcyclopentadienyl | | Dimethylphosphido | | 1,2-bis(trimethyl-silazene)ethane |
| Methylphosphinediyl | Indenyl | | | | 1,1,4,4-tetra-methyldisilyl-ethylene |
| Ethylphosphinediyl | Tetrahydroindenyl | | (both X) | | Dimethyl-germylene |
| Phenylphosphinediyl | 4-phenylindenyl | | methylidene | | Tetramethyl-digermylene |
| t-butylphosphinediyl | | | ethylidene | | Phenylazanediyl |
| (formulae A, C) | (x = 3) | | propylidene | | t-butylazanediyl |
| Methylsilanetriyl | 2-methylindenyl | | propylene | | Methylazanediyl |
| Ethylsilanetriyl | 3-methylindenyl | | butylene | | Ethylphosphine-diyl |
| n-propylsilanetriyl | 2-methyl-4-phenylindenyl | | pentylene | | t-butylphosphine-diyl |
| Isopropylsilanetriyl | 2-methyl-4-napthaylindenyl | | 1,3-butadiene | | Pheynlphosphine-diyl |
| | 2-isopropylindenyl | Diphenylamido | 2,4-dimethyl-1,3-butadiene | | Phenylboranediyl |
| n-butylsilanetriyl | 2-isopropyl-4-phenylindenyl | di-p-n-butylphenylamido | 1,3-pentadiene | | t-butylboranediyl |

TABLE 1-continued

| T | $(C_5H_{5-x-y}R_x)$, or $(C_5H_{4-x}R_x)$ | $(JU'_{z-2})$, $(JR'_{z-2-y})$, or J | X | M | Q* |
|---|---|---|---|---|---|
| t-butylsilanetriyl | 2-methyl-4-napthaylindenyl | Diperfluorophenylasnido | 1,4-pentadiene | | Methylboranediyl |
| n-hexylsilanetriyl | 1,2,4-triphenylcyclopentadienyl | Dicyclohexylamido | 1,3-hexadiene | | Ethylboranediyl |
| Phenylsilanetriyl | | Dicyclooctylamido | 1,4-hexadiene | | Oxo |
| Methylgermanetriyl | (x = 4) | Dicyclodecylamido | 1,5-hexadiene | | Thio |
| Phenylgermanetriyl | Tetramethylcylopentadienyl | Dicyclododecylamido | 2,4-hexadiene | | |
| Azanetriyl | Tetraphenylcyclopentadienyl | di-2-norbonsylamido | 2-methyl-1,3-hexadiene | | |
| Phosphinetriyl | 2,3-dimethylindenyl | di-1-adamantylamido | 2-methyl-1,3-pentadiene | | |
| | 2-methyl-3-ethylindenyl | Methyladamantylamido | | | |
| | 2,3,4,6-tetramethylindenyl | Methylcylcohexylamido | | | |
| | 2,3,4,6,7-pentamethylindenyl | Methylcyclododecylamido | | | |
| | Fluorenyl | Methyl-t-butylamido | | | |
| | Octahydrofluorenyl | Diphenylphosphido | | | |
| | 2,7-di-t-butylfluorenyl | di-t-butylphosphido | | | |
| | (x = 5) | (fromulae B (y = 1), & F) | | | |
| | Pentamethylcyclopentadienyl | Amido | | | |
| | | Phosphido | | | |

*Restrictions for Q when bonded to two T are found on page 6, ilines 22–30

Metal complexes according to the invention can be prepared by various synthetic routes. Exemplary synthesis routes are illustrated in FIGS. 2–5, which show the preparation of compounds of formula A, B (y=1), B (y=0), and C, respectively.

In FIGS. 2–5, $(C_5H_{5-x-y}R_x)$, $(C_5H_{4-x}R_x)$, R, R', J, T, M, Q, x, y & z are as previously defined; H is hydrogen; A is a Group 1 metal such as Li or K, or a Grignard reagent such as MgCl or MgBr; each X' is independently a halogen, especially Cl and Br, or X as previously described, provided that at least two X' are halogen and that X" is halogen when bonded to T; each X" is independently an amide ligand such as $NMe_2$ or $NEt_2$ and the like, or X as previously described, provided that at least two X" are an amide ligand; each X''' is X' if reaction Step 4A, 5B, or 4C is used or X" if reaction Step 4A', 5B', or 4C' is used; and R* is a hydrocarbyl especially methyl and n-butyl.

In the preparation of Compounds of Formula A, Steps 1A and 2A are preferred over Steps 1A' and 2A' unless R' is a very bulky substituent. In both Steps 1A and 1A', it is preferable to slowly add the salt to the $(X')_2T—Q—T(X')_2$ solution, verses the reverse addition order. In both Steps 4A and 4A', it is preferable to add the $MX'_4$ or $MX''_4$, respectively, to a dilute solution of the cyclopentadienyl-containing reactant to maximize the yield of the final product.

In the preparation of Compounds of Formula B when y=1, in both Steps 5B and 5B', it is preferable to add the $MX'_4$ or $MX''_4$, respectively, to a dilute solution of the cyclopentadienyl-containing reactant to maximize the yield of the final product.

In the preparation of Compounds of Formula B when y=0, in Step 3B", it is preferable to add the salt to a concentrated solution of $(C_5H_{5-x}R_x)MX'_3$ to maximize the yield of the final product.

In the preparation of Compounds of Formula C, Steps 1C and 2C are preferred over Steps 1C' and 2C'. In Step 2C, it is preferable to add the salt to a very dilute solution of the cyclopentadienyl-containing reactant, or in the case where the salt has greater solubility in a given solvent than the cyclopentadienyl-containing reactant, it is preferable to add the cyclopentadienyl-containing reactant to a very dilute solution of the salt. In Step 1C', it is preferable to add the salt to a very dilute solution $(X')_2T—Q—T(X')_2$, or in the case where the salt has greater solubility in a given solvent than $(X')_2T—Q—T(X')_2$, it is preferable to add $(X')_2T—Q—T(X')_2$ to a very dilute solution of the salt. In both Steps 4C and 4C', it is preferable to add the $MX'_4$ or $MX''_4$, respectively, to a dilute solution of the cyclopentadienyl-containing reactant to maximize the yield of the final product.

A concentrated solution is defined from the saturation point of a compound in a solvent up to about 1 g of compound per 10 ml of solution, more preferably from the saturation point of a compound in a solvent up to about 1 g of compound per 5 ml of solution. A dilute solution is defined from about 1 g of compound per 10 ml of solution to about 1 g of compound per 100 ml of solution, more preferably from about 1 g of compound per 20 ml of solution to about 1 g of compound per 75 ml of solution. A very dilute solution is defined from about 1 g of compound per 100 ml of solution to about 1 g of compound per 2000 ml of solution, more preferably from about 1 g of compound per 200 ml of solution to about 1 g of compound per 2000 ml of solution.

The metal compounds according to the invention may be activated for insertion polymerization catalysis by known methods for metallocene transition metal compounds suitable for coordination polymerization. This activation is achieved for coordination polymerization by the inclusion of at least one reactive metal-ligand sigma bonded ligand and at least one single vacant orbital adjacent (cis) to the sigma bonded ligand, as is achieved by activation. The traditional activators of metallocene coordination polymerization art are suitable, those typically including alumoxane compounds, modified alumoxane compounds, and ionizing, anion precursor compounds that abstract one ligand so as to ionize the metal center into a cationic complex and provide a counter-balancing weakly or noncoordinating anion, which can optionally be bound to the cationic complex so as to form a Zwitterionic catalyst.

Alkylalumoxanes and modified alkylalumoxanes are suitable as catalyst activators, particularly for the invention metal compounds comprising halide ligands. The alumoxane component useful as catalyst activator typically is an oligomeric aluminum compound represented by the general formula $(R^2—Al—O)_m$, which is a cyclic compound, or $R^3(R^4—Al—O)_mAlR^5$, which is a linear compound, although other structural variations may exist. In the general alumoxane formula each $R^2—R^5$ is independently a $C_1$ to $C_{10}$ hydrocarbyl radical, for example, methyl, ethyl, and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, and n is an integer from 1 to about 50. Most preferably, $R^2$—$R^5$ is methyl and m is at least 4. Alumoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an alumoxane. Generally, however prepared, the reaction of an aluminum alkyl with a limited amount of water yields a mixture of the linear and cyclic species of the alumoxane. Methylalumoxane and modified methylalumoxanes are preferred. Mixtures of different alumoxanes and modified alumoxanes may also be used. Additionally, solid alumoxanes prepared by removing solvent and volatile components from liquid alumoxanes may also be used either as a solid or as a reconstituted solution or mixture. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516476 A, EP 0 594 218 A1 and WO 94/10180, each being incorporated by reference for purposes of U.S. patent practice.

When the activator is an alumoxane, the preferred transition metal compound to activator molar ratio is from about 1:5000 to 1:1, more preferably from about 1:1000 to 1:10, even more preferably from about 1:500 to 1:10 and most preferably from about 1:100 to 1:10.

The term "noncoordinating anion" is recognized to mean an anion which either does not coordinate to the metal cation or which is only weakly coordinated to it thereby remaining sufficiently labile to be displaced by a neutral Lewis base, such as an olefinically or acetylenically unsaturated monomer.

Descriptions of ionic catalysts, those comprising a transition metal cationic complex and a noncoordinating anion, suitable for coordination polymerization appear in the early work in U.S. Pat. Nos. 5,064,802, 5,132,380, 5,198,401, 5,278,119, 5,321,106, 5,347,024, 5,408,017, 5,599,671, and WO 92/00333 and WO 93/14132. These teach a preferred method of preparation wherein metallocenes are protonated by noncoordinating anion precursors such that an alkyl/hydride group is abstracted by protonation from a transition metal to make it both cationic and charge-balanced by the noncoordinating anion. Since the abstraction and insertion ligands of such metallocenes also may be ligands of the metal compounds of the invention, similar methods of preparation as active polymerization catalyst components may be followed.

The use of ionizing ionic compounds not containing an active proton but capable of producing both an active metal cationic complex and a noncoordinating anion is also possible. See, EP-A-0 426 637, EP-A-0 573 403 and U.S. Pat. No. 5,387,568 for instructive ionic compounds. Reactive cations of the ionizing ionic compounds, other than the Bronsted acids, include ferrocenium, silver, tropylium, triphenylcarbenium and triethylsilylium, or alkali metal or alkaline earth metal cations such as sodium, magnesium or lithium cations. A further class of noncoordinating anion precursors suitable in accordance with this invention are hydrated salts comprising the alkali metal or alkaline earth metal cations and a non-coordinating anion as described above. The hydrated salts can be prepared by reaction of the metal cation-noncoordinating anion salt with water, for example, by hydrolysis of the commercially available or readily synthesized LiB(pfp)$_4$ which yields [Li(H$_2$O)$_x$][B(pfp)4], where (pfp) is pentafluorophenyl or perfluorophenyl.

Any metal or metalloid capable of forming a coordination complex which is resistant to degradation by water (or other Bronsted or Lewis Acids) may be used or contained in the noncoordinating anion. Suitable metals include, but are not limited to, aluminum, gold, platinum and the like. Suitable metalloids include, but are not limited to, boron, phosphorus, silicon and the like. The description of noncoordinating anions and precursors thereto of the documents of the foregoing paragraphs are incorporated by reference for purposes of U.S. patent practice.

An additional method of making the active polymerization catalysts of this invention uses ionizing anion precursors which are initially neutral Lewis acids but form a metal cationic complex and the noncoordinating anion, or a Zwitterionic complex upon the ionizing reaction with the invention compounds, for example tris(pentafluorophenyl) boron or aluminum act to abstract a hydrocarbyl or hydride ligand to yield an invention metal cationic complex and stabilizing noncoordinating anion, see EP-A-0 427 697 and EP-A-0 520 732 for illustration utilizing analogous Group 4 metallocene compounds. See also the methods and compounds of EP-A-0 495 375. For formation of Zwitterionic complexes see U.S. Pat. Nos. 5,624,878; 5,486,632; and 5,527,929. The description of noncoordinating anions and precursors thereto of these documents are similarly incorporated by reference for purposes of U.S. patent practice. When the activator is a neutral Lewis acid (other than an alumoxane or modified alumoxane), the transition metal to activator molar ratio may be any ratio but preferably from about 10:1 to 1:10, more preferably from about 5:1 to 1:5, even more preferably from about 2:1 to 1:2 and most preferably from about 1.2:1 to 1:1.2 with the ratio of about 1:1 being the most preferred.

When the cation portion of an ionic noncoordinating anion precursor is a Bronsted acid such as protons or protonated Lewis bases (excluding water), or a reducible Lewis acid such as ferrocenium or silver cations, or alkali metal or alkaline earth metal cations such as those of sodium, magnesium or lithium cations, the transition metal to activator molar ratio may be any ratio, but preferably from about 10:1 to 1:10, more preferably from about 5:1 to 1:5, even more preferably from about 2:1 to 1:2 and most preferably from about 1.2:1 to 1:1.2 with the ratio of about 1:1 being the most preferred.

Combinations of the activator compounds described may also be used for activation. For example, tris(perfluorophenyl) boron can be used in conjunction with methylalumoxane.

When the X ligands are not hydride, hydrocarbyl or hydrocarbylsilyl and are not capable of discrete ionizing abstraction with the ionizing, anion precursor compound, the X ligands can be converted via known alkylation reactions with organometallic compounds such as lithium or aluminum hydrides or alkyls, alkylalumoxanes or alkyl aluminum compounds, Grignard reagents, etc. See EP-A-0 500 944, EP-A1-0 570 982 and EP-A1-0 612 768 for processes describing the reaction of alkyl aluminum compounds with dihalide substituted metallocene compounds prior to or with the addition of activating noncoordinating anion precursor compounds.

The catalyst complexes of the invention are useful in polymerization of unsaturated monomers conventionally known to be polymerizable under coordination polymerization conditions using metallocenes. Such conditions are well known and include solution polymerization, slurry polymerization, gas-phase polymerization, and high pressure polymerization. The catalyst of the invention may be supported and as such will be particularly useful in the known operating modes employing fixed-bed, moving-bed, fluid-bed, slurry or solution processes conducted in single, series or parallel reactors.

When using the catalysts of the invention, particularly when immobilized on a support, the total catalyst system will generally additionally comprise one or more scavenging compounds. The term "scavenging compounds" as used in this application and its claims is meant to include those compounds effective for removing polar impurities from the reaction environment. Impurities can be inadvertently introduced with any of the polymerization reaction components, particularly with solvent, monomer and catalyst feed, and adversely affect catalyst activity and stability. It can result in decreasing or even elimination of catalytic activity, particularly when ionizing anion pre-cursors activate the catalyst system. The polar impurities, or catalyst poisons include water, oxygen, metal impurities, etc. Preferably steps are taken before provision of such into the reaction vessel, for example by chemical treatment or careful separation techniques after or during the synthesis or preparation of the various components, but some minor amounts of scavenging compound will still normally be used in the polymerization process itself.

Typically the scavenging compound will be an organometallic compound such as the Group 13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, isobutyl aluminumoxane, and tri-n-octyl aluminum. Those scavenging compounds having bulky or $C_6$–$C_{20}$ linear hydrocarbyl substituents covalently bound to the metal or metalloid center are preferred to minimize adverse interaction with the active catalyst. Examples include triethylaluminum, but more preferably, bulky compounds such as triisobutylaluminum, triisoprenylaluminum, and long-chain linear alkyl-substituted aluminum compounds, such as tri-n-hexylaluminum, tri-n-octylaluminum, or tri-n-dodecylaluminum. When alumoxane is used as activator, any excess over the amount needed to activate the catalysts present will act as scavenger compounds and additional scavenging compounds may not be necessary. Alumoxanes also may be used in scavenging amounts with other means of activation, e.g., [$Me_2BPh$][$B(pfp)4$] or $B(pfp)_3$. The amount of scavenging agent to be used with the catalyst compounds of the invention is minimized during polymerization reactions to that amount effective to enhance activity and avoided altogether if the feeds can be sufficiently free of adventitious impurities.

The catalyst according to the invention may be supported for use in gas phase, bulk, slurry polymerization processes, or otherwise as needed. Numerous methods of support are known in the art for copolymerization processes for olefins, particularly for catalysts activated by alumoxanes, any is suitable for the invention process in its broadest scope. See, for example, U.S. Pat. Nos. 5,057,475 and 5,227,440. An example of supported ionic catalysts appears in WO 94/03056. A particularly effective method is that described U.S. Pat. No. 5,643,847, and WO 96/04319. A bulk, or slurry, process utilizing supported, invention metal compounds activated with alumoxane co-catalysts can be utilized as described for ethylene-propylene rubber in U.S. Pat. Nos. 5,001,205 and 5,229,478, and these processes will additionally be suitable with the catalyst systems of this application. Both inorganic oxide and polymeric supports may be utilized in accordance with the knowledge in the field. See U.S. Pat. Nos. 5,422,325, 5,427,991, 5,498,582 and 5,466,649, and international publications WO 93/11172 and WO 94/07928. Each of the foregoing documents is incorporated by reference for purposes of U.S. patent practice.

In preferred embodiments of the process for this invention, the catalyst system is employed in liquid phase (solution, slurry, suspension, bulk phase or combinations thereof), in high pressure liquid or supercritical fluid phase, or in gas phase. Each of these processes may be employed in singular, parallel or series reactors. The liquid processes comprise contacting olefin monomers with the above described catalyst system in a suitable diluent or solvent and allowing said monomers to react for a sufficient time to produce the invention copolymers. Hydrocarbyl solvents are suitable, both aliphatic and aromatic, hexane and toluene are preferred. Bulk and slurry processes are typically done by contacting the catalysts with a slurry of liquid monomer, the catalyst system being supported. Gas phase processes typically use a supported catalyst and are conducted in any manner known to be suitable for ethylene homopolymers or copolymers prepared by coordination polymerization. Illustrative examples may be found in U.S. Pat. Nos. 4,543,399, 4,588,790, 5,028,670, 5,382,638, 5352,749, 5,436,304, 5,453,471, and 5,463,999, and WO 95/07942. Each is incorporated by reference for purposes of U.S. patent practice.

Generally speaking the polymerization reaction temperature can vary from about −50° C. to about 250° C. Preferably the reaction temperature conditions will be from −20° C. to 220°, more preferably below 200° C. The pressure can vary from about 1 mm Hg to 2500 bar, preferably from 0.1 bar to 1600 bar, most preferably from 1.0 to 500 bar.

Linear polyethylene, including high and ultra-high molecular weight polyethylenes, including both homo- and copolymers with other alpha-olefin monomers, alpha-olefinic and/or non-conjugated diolefins, for example, $C_3$–$C_{20}$ olefins, $C_4$–$C_{20}$ diolefins, $C_4$–$C_{20}$ cyclic olefins or $C_8$–$C_{20}$ styrenic olefins, are produced by adding ethylene, and optionally one or more of the other monomers, to a reaction vessel at a typical temperature of 20–250° C. with the invention catalyst that has been slurried with or dissolved in a solvent, such as hexane or toluene. Heat of polymerization is typically removed by cooling. Gas phase polymerization can be conducted, for example, in a continuous fluid bed gas-phase reactor operated at about 200–3000 kPa and 60–160° C., using hydrogen as a reaction modifier (100–200 ppm), $C_4$–$C_8$ comonomer feedstream (0.5–12 mol %), and $C_2$ feedstream (25–35 mol %). See, U.S. Pat. Nos. 4,543,399, 4,588,790, 5,028,670 and 5,405,922 and 5,462,999, which are incorporated by reference for purposes of U.S. patent practice.

Ethylene-α-olefin (including ethylene-cyclic olefin and ethylene-α-olefin-diolefin) elastomers of high molecular weight and low crystallinity can be prepared utilizing the catalysts of the invention under traditional solution polymerization processes or by introducing ethylene gas into a slurry utilizing the α-olefin or cyclic olefin or mixture thereof with other monomers, polymerizable and not, as a polymerization diluent in which the invention catalyst is suspended. Typical ethylene pressures will be between 10 and 1000 psig (69–6895 kPa) and the polymerization diluent temperature will typically be between −10 to 160° C. The process can be carried out in a stirred tank reactor, or more than one reactor operated in series or parallel. See the general disclosure of U.S. Pat. No. 5,001,205 which is incorporated by reference for its description of polymerization processes, ionic activators and useful scavenging compounds.

Pre-polymerization of the supported catalyst of the invention may also be used for further control of polymer particle morphology in typical slurry or gas phase reaction processes in accordance with conventional teachings. For example, such can be accomplished by pre-polymerizing a $C_2$–$C_6$ α-olefin for a limited time, for example, ethylene is contacted with the supported catalyst at a temperature of −15° to 30° C. and ethylene pressure of up to about 250 psig (1724 kPa) for 75 min to obtain a polymeric coating on the support of polyethylene of 30,000–150,000 molecular weight. The pre-polymerized catalyst is then available for use in the polymerization processes referred to above. The use of polymeric resins as a support coating may additionally be utilized, typically by suspending a solid support in dissolved resin of such material as polystyrene with subsequent separation and drying.

Other olefinically unsaturated monomers besides those specifically described above may be polymerized using the catalysts according to the invention, for example, isobutylene, styrene, alkyl-substituted styrene, ethylidene norbornene, norbornadiene, dicyclopentadiene, vinylcyclohexane, vinylcyclohexene, isobutylene, 2-butene and other olefinically-unsaturated monomers, including other cyclic olefins, such as cyclopentene, norbornene, and alkyl-substituted norbornenes. Additionally, α-olefinic macromonomers of up to 1000 mer units, or more, may also be incorporated by copolymerization.

The catalyst compositions of the invention can be used as described above individually for coordination polymerization or can be mixed to prepare polymer blends with other known olefin polymerization catalyst compounds. By selection of monomers, blends of coordination catalyst compounds, polymer blends can be prepared under polymerization conditions analogous to those using individual catalyst compositions. Polymers having increased MWD for improved processing and other traditional benefits available from polymers made with mixed catalyst systems can thus be achieved.

EXAMPLES

The following examples are presented to illustrate the foregoing discussion. All parts, proportions, and percentages are by weight unless otherwise indicated. All reactions and manipulations have been conducted using dry, oxygen-free solvents under an inert nitrogen atmosphere. Although the examples may be directed toward certain embodiments of the present invention, they are not to be viewed as limiting the invention in any specific respect. In these examples, certain abbreviations are used to facilitate the description. These include standard chemical abbreviations for the elements and certain commonly accepted abbreviations, such as: Me=methyl, Et=ethyl, Bu=butyl, Ph=phenyl, MAO=methylalumoxane, and TBF=tetrahydrofuran. Abbreviations used in the accompanying tables include S=single, M=multiple, Cn=Comonomer, T=temperature, P=pressure, t=time, TMC=transition metal complex, P=polymer yield, Br=short chain branches per 1000 C atoms as measured by proton NMR, rl=pseudo "$r_1$" value indicating the probability of a comonomer inserting into a growing polymer chain regardless of the last monomer to have inserted, Vi1=vinylene endgroup unsaturation per 1000 carbon atoms as measured by proton NMR, Tri=trisubstituted endgroup unsaturation in the polymer per 1000 carbon atoms as measured by proton NMR, Vi2=vinyl endgroup unsaturation in the polymer per 1000 carbon atoms as measured by proton NMR, and Vi3=vinylidene endgroup unsaturation in the polymer per 1000 carbon atoms as measured by proton NMR.

All molecular weights are weight average molecular weight unless otherwise noted. Molecular weights (weight average molecular weight ($M_w$) and number average molecular weight ($M_n$)) were measured by Gel Permeation Chromatography, unless otherwise noted, using a Waters 150 Gel Permeation Chromatograph equipped with a differential refractive index detector and calibrated using polystyrene standards. Samples were run in either TBF (45° C.) or in 1,2,4-trichlorobenzene (145° C.) depending upon the sample's solubility using three Shodex GPC AT-80 M/S columns in series. This general technique is discussed in "Liquid Chromatography of Polymers and Related Materials III" J. Cazes Ed., Marcel Decker, 1981, page 207, which is incorporated by reference for purposes of U.S. patent practice herein. No corrections for column spreading were employed; however, data on generally accepted standards, e.g. National Bureau of Standards Polyethylene 1475, demonstrated a precision with 0.1 units for $M_w/M_n$ which was calculated from elution times. The numerical analyses were performed using Expert Ease® software available from Waters Corporation.

All procedures were performed under an inert atmosphere of nitrogen. Solvent choices are often optional, for example, in most cases either pentane or 30–60 petroleum ether can be interchanged. The lithiated amides were prepared form the corresponding amines and either n-BuLi or MeLi. Published methods for preparing $LiHC_5Me_4$ include C. M. Fendrick et al. *Organometallics,* 3, 819 (1984) and F. H. Köhler and K. H. Doll, *Z. Naturforsch,* 376, 144 (1982). Other lithiated substituted cyclopentadienyl compounds are typically prepared from the corresponding cyclopentadienyl ligand and n-BuLi or MeLi, or by reaction of MeLi with the proper fulvene. $ZrCl_4$, $HfCl_4$ and $TiCl_4$ were purchased from either Cerac, or Aldrich Chemical Company. $TiCl_4$ was typically used in its etherate form. The etherate, $TiCl_4.2Et_2O$ can be prepared by gingerly adding $TiCl_4$ to diethyl ether. Amines, silanes and lithium reagents were purchased from Aldrich Chemical Company or United Chemical Technologies. Methylalumoxane was supplied by Albemarle Corporation.

Example 1

Preparation of $[Cl_2Hf(Me_4C)(N-t-Bu)Si(Me)]_2(CH)6$ (I).

To approximately 150 ml of THF, 1,6-bis (dichloromethylsilyl)hexane (18.8 g, 0.060 mol) was added. To this, lithiated tetramethylcyclopentadiene (15.0 g, 0.12 mol) was added and the reaction was allowed to stir for three hours. The THF was removed via vacuum and petroleum ether was added to the flask. The contents were filtered through Celite® and the filtrate was reduced in volume to the point where the product began to crystallize out of solution. The flask was then placed in a refrigerator at −30° C. to aid crystallization of the product. After several hours of chilling, the solid was filtered off and dried under vacuum. $(Me_4C_5H)(Me)(Cl)Si(CH_2)_6Si(Me)(Cl)(Me_4C_5H)$ was obtained (18.6 g).

$(Me_4C_5H)(Me)(Cl)Si(CH_2)_6Si(Me)(Cl)(Me_4C_5H)$ (5.0 g, 0.010 mol) was added to approximately 150 ml of the TBF. To this, lithiated t-butylamine (1.68 g, 0.21 mol) was added and the reaction mixture was allowed to stir for 2 hours. The solvent was then removed via vacuum, approximately 150 ml of diethyl ether and 29.6 ml (0.041 mol) of 1.4 M MeLi in diethyl ether was added and the reaction mixture was allowed to stir for three hours. The reaction flask was then chilled to −30° C. and 6.4 g (0.020 mol) of $HfCl_4$ were slowly added. This mixture was allowed to stir overnight. The solvent was then removed via vacuum and methylene chloride was added to dissolve the product. The mixture was filtered to remove the LiCl. The filtrate was reduced in volume and placed in a refrigerator at −30° C. to induce crystallization. After several hours, the crude product was filtered off. This solid was recrystallized twice; the first time from toluene and the second time from pentane. The product, [Cl$_2$Hf(Me$_4$C$_5$)(N-t-Bu)Si(Me)]$_2$(CH$_2$)$_6$, was obtained as a white solid in a yield of 1.93 g.

Example 2

Preparation of m-[Cl$_2$Ti(Me$_4$C$_5$)Si(Me)$_2$(N)]$_2$C$_6$H$_4$ (II).

Dichlorodimethylsilane (13 g, 0.10 mol) was diluted with approximately 200 ml of THF. To this, 10.5 g (0.082 mol) of lithiated tetramethylcyclopentadiene were slowly added and the mixture was allowed to stir for three hours. The solvent was removed via vacuum and petroleum ether was added. The mixture was filtered through Celite® to remove the LiCl. The solvent was removed from the filtrate, leaving behind the yellow liquid, (Me$_4$CH)Si(Me)$_2$Cl (16.7 g).

(Me$_4$C$_5$H)Si(Me)$_2$Cl (6.0 g, 0.028 mol) was diluted with approximately 150 ml of THF. To this, 1.67 g (0.014 mol) of dilithiated 1,3-phenyldiamine was added and the mixture and was allowed to stir for three hours. The solvent was removed via vacuum and petroleum ether was added. The mixture was filtered through Celite® to remove the LiCl. The solvent was removed from the filtrate to produce 1.6 g of the product, m-[(Me$_4$C$_5$H)Si(Me)$_2$(NH)]$_2$C$_6$H$_4$.

To m-[(Me$_4$C$_5$H)Si(Me)$_2$(NH)]$_2$C$_6$H$_4$ (11.6 g, 0.025 mol), approximately 150 ml of diethyl ether was added. To this, 71 ml (0.099 mol) of 1.4 M MeLi in diethyl ether was added and the reaction mixture was allowed to stir for three hours. The mixture was filtered, and the solid was dried yielding 8.4 g of m-[(Me$_4$C$_5$Li)Si(e)$_2$(NLi)]$_2$C$_6$H$_4$.

m-[(Me$_4$C$_5$Li)Si(Me)(NLi)]$_2$C$_6$H$_4$ (4.2 g, 0.0088 mol) was added to approximately 200 ml of diethyl ether. To this, 5.81 g (0.0172 mol) of TiCl$_4$.2Et$_2$O was slowly added and the reaction was allowed to stir overnight. The solvent was removed via vacuum and pentane was added. The mixture was filtered through Celite® to remove the LiCl. The filtrate was reduced in volume via vacuum and the flask was placed in a refrigerator at −30° C. to induce crystallization. After several hours, the product was filtered off, washed with cold pentane and dried. m-[Cl$_2$Ti(Me$_4$C$_5$)Si(Me)$_2$(N)]$_2$C$_6$H$_4$ was isolated as a bright orange solid (0.45 g).

Example 3

Preparation of [Cl$_2$Ti(Me$_4$C$_5$)Si(Me)$_2$(N)]$_2$C$_{12}$H$_{24}$ (III).

(Me$_4$C$_5$H)Si(Me)$_2$Cl (6.0 g, 0.028 mol) was diluted with approximately 150 ml of THF. To this, 2.96 g (0.014 mol) of dilithiated 1,12diaminododecane was added and the mixture was allowed to stir for two hours. The solvent was removed via vacuum and petroleum ether was added. The mixture was filtered through Celite® to remove the LiCl. The solvent was removed from the filtrate to produce 14.0 g of the product, [(Me$_4$C$_5$H)Si(Me)$_2$(NH)]$_2$C$_{12}$H$_{24}$.

To approximately 250 ml of diethyl ether, 14.0 g (0.025 mol) of [(Me$_4$C$_5$H)Si(Me)$_2$(NH)]$_2$C$_{12}$H$_{24}$ were added. To this, 71.7 ml (0.100 mol) of 1.4 M MeLi in diethyl ether was added and the mixture was allowed to stir for four hours. The mixture was filtered and the collected solid dried to yield 14.0 g of [(Me$_4$C$_5$Li)Si(Me)$_2$(NLi)]$_2$C$_{12}$H$_{24}$.

To approximately 250 ml of diethyl ether, 3.8 g (0.0067 mol) of [(Me$_4$C$_5$Li)Si(Me)$_2$(NLi)]$_2$C$_{12}$H$_{24}$ was added. To this, 4.4 g (0.013 mol) of TiCl$_2$.2Et$_2$O was added and the reaction mixture was allowed to stir overnight. The solvent was removed via vacuum and pentane was added. The mixture was filtered through Celite® to remove the LiCl. The filtrate was reduced in volume and the flask was placed in a refrigerator at −30° C. to induce crystallization. After several hours, the product was filtered off and washed with cold pentane. The product, [Cl$_2$Ti(Me$_4$C$_5$)Si(Me)$_2$(N)]$_2$C$_{12}$H$_{24}$ was isolated as a yellow solid (0.48 g).

Examples 4–31

Olefin Polymerization with the Catalyst Complexes of Examples 1–3.

Polymerization runs with the catalyst precursors of Examples 1–3 were performed in either a 1-liter or ½-liter autoclave reactor equipped with a paddle stirrer, an external water jacket for temperature control, a regulated supply of dry nitrogen and ethylene, addition ports for propylene, 1-butene and hexane, and a septum inlet for introduction of other solvents or comonomers, transition metal compound and alumoxane solutions. The reactor was dried and degassed thoroughly prior to use.

For the 1-liter reactor, a typical run consisted of injecting solvent, comonomer if used, alumoxane, and a stock solution of the transition metal complex (TMC) into the reactor. The reactor was typically heated prior to the introduction of the TMC, and the ethylene (if used) was introduced into the system semi-continuously to maintain reactor pressure. The polymerization reaction was limited to the indicated time. The reaction was ceased by rapidly cooling and venting the system and the solvent was evaporated off of the polymer by a stream of nitrogen.

The use of the ½-liter reactor was similar to the 1-liter reactor, with exception of the option of semi-continuously injecting transition metal compound into the reactor. The details of the polymerization runs are set forth in Table 2.

TABLE 2

| Example # | TMC | Type of Run | Reactor size (L) | TMC Stock (mg/ml) | TMC Stock used (ml) | Single or Multiple TMC Addition | 10 wt % MAO (ml) | Al/M Ratio | Type | Solvent (ml) | Cn (ml) | T (C) | C2 = (psid) | Time (hr) |
|---|---|---|---|---|---|---|---|---|---|---|---|---|---|---|
| 4 | I | C$_2$ | 1 | 2.2 | 1.0 | S | 3.0 | 1435 | hexane | 400 | 0 | 80 | 40 | 1 |
| 5 | I | C$_2$ | 1 | 1.5 | 0.2 | S | 3.0 | 10520 | toluene | 400 | 0 | 80 | 40 | 1 |
| 6 | II | C$_2$ | 1 | 0.9 | 0.2 | S | 3.0 | 11640 | toluene | 400 | 0 | 80 | 40 | 1 |
| 7 | III | C$_2$ | 1 | 1.1 | 0.2 | S | 3.0 | 10782 | toluene | 400 | 0 | 80 | 40 | 1 |
| 8 | I | C$_2$ | 1 | 1.5 | 0.2 | S | 3.0 | 10520 | toluene | 400 | 0 | 80 | 65 | 0.25 |
| 9 | I | C$_2$ | 0.5 | 0.1 | 49.0 | M | 2.5 | 516 | toluene | 250 | 0 | 60 | 50 | 0.5 |
| 10 | II | C$_2$ | 0.5 | 0.1 | 12.6 | M | 2.5 | 2777 | toluene | 250 | 0 | 60 | 51 | 0.5 |
| 11 | II | C$_2$ | 0.5 | 0.2 | 10.0 | S | 1.4 | 535 | toluene+ | 250 | 0 | 60 | 51 | 0.5 |
| 12 | III | C$_2$ | 0.5 | 0.0 | 37.0 | M | 2.5 | 1336 | toluene | 250 | 0 | 60 | 50 | 0.5 |
| 13 | III | C$_2$ | 0.5 | 0.4 | 5.9 | S | 1.6 | 534 | toluene+ | 250 | 0 | 60 | 53 | 0.5 |
| 14 | II | C$_2$ | 0.5 | 0.1 | 15.1 | M | 2.5 | 2313 | toluene | 250 | 0 | 90 | 81 | 0.5 |
| 15 | II | C$_2$ | 0.5 | 0.2 | 8.0 | S | 1.4 | 532 | toluene+ | 250 | 0 | 90 | 71 | 0.5 |
| 16 | III | C$_2$ | 0.5 | 0.1 | 6.6 | M | 2.5 | 2665 | toluene | 250 | 0 | 90 | 74 | 0.5 |

TABLE 2-continued

| Example # | TMC | Type of Run | Reactor size (L) | TMC Stock (mg/ml) | TMC Stock used (ml) | Single or Multiple TMC Addition | 10 wt % MAO (ml) | Al/M Ratio | Type | Solvent (ml) | Cn (ml) | T (C) | C2= (psid) | Time (hr) |
|---|---|---|---|---|---|---|---|---|---|---|---|---|---|---|
| 17 | III | C$_2$ | 0.5 | 0.3 | 8.0 | S | 1.8 | 678 | toluene+ | 250 | 0 | 90 | 72 | 0.5 |
| 18 | III | C$_2$ | 0.5 | 0.1 | 24.0 | M | 2.5 | 792 | toluene | 250 | 0 | 120 | 40 | 1 |
| 19 | III | C$_2$ | 0.5 | 0.7 | 8.0 | S | 2.0 | 304 | toluene+ | 250 | 0 | 120 | 43 | 1 |
| 20 | III | C$_2$/C$_4$ | 1 | 1.1 | 2.0 | S | 3.0 | 1078 | toluene | 400 | 25 | 80 | 65 | 0.25 |
| 21 | II | C$_2$/C$_6$ | 1 | 1.0 | 2.0 | S | 3.0 | 1048 | toluene | 350 | 50 | 80 | 65 | 0.25 |
| 22 | III | C$_2$/C$_6$ | 1 | 1.1 | 2.0 | S | 3.0 | 1078 | toluene | 350 | 50 | 80 | 65 | 0.25 |
| 23 | II | C$_2$/C$_6$ | 0.5 | 0.1 | 38.0 | M | 2.5 | 459 | toluene | 250 | 14.8 | 60 | 50 | 0.5 |
| 24 | II | C$_2$/C$_6$ | 0.5 | 0.4 | 10.0 | S | 3.0 | 524 | toluene+ | 250 | 14.8 | 60 | 49 | 0.5 |
| 25 | III | C$_2$/C$_6$ | 0.5 | 0.1 | 16.0 | M | 2.5 | 1187 | toluene | 250 | 14.8 | 60 | 49 | 0.5 |
| 26 | III | C$_2$/C$_6$ | 0.5 | 0.4 | 8.0 | S | 1.5 | 395 | toluene+ | 250 | 14.8 | 60 | 49 | 0.5 |
| 27 | III | C$_2$/C$_6$ | 0.5 | 0.4 | 8.0 | S | 1.8 | 474 | toluene+ | 250 | 14.8 | 60 | 50 | 0.5 |
| 28 | II | C$_2$/C$_6$ | 0.5 | 0.1 | 38.0 | M | 2.5 | 371 | toiuene | 250 | 15.3 | 90 | 71 | 0.5 |
| 29 | II | C$_2$/C$_6$ | 0.5 | 0.6 | 10.0 | S | 3.0 | 374 | toluene+ | 250 | 15.3 | 90 | 68 | 0.5 |
| 30 | III | C$_2$/C$_6$ | 0.5 | 0.1 | 15.8 | M | 2.5 | 1199 | toluene | 250 | 15.3 | 90 | 71 | 0.5 |
| 31 | III | C$_2$/C$_6$ | 0.5 | 0.4 | 8.0 | S | 1.8 | 474 | toluene+ | 250 | 15.3 | 90 | 71 | 0.5 |
| 32 | II | C$_3$ | 1 | 1.4 | 1.0 | S | 2.0 | 1497 | none | 0 | 400 | 40 | 0 | 1 |
| 33 | II | C$_3$ | 1 | 1.4 | 1.0 | S | 2.0 | 1497 | none | 0 | 400 | 40 | 0 | 1 |
| 34 | III | C$_3$ | 1 | 1.6 | 1.0 | S | 2.0 | 1482 | none | 0 | 400 | 40 | 0 | 1 |
| 35 | I | C$_3$ | 1 | 2.2 | 1.0 | S | 2.0 | 1435 | none | 0 | 400 | 40 | 0 | 1 |
| 36 | II | C$_3$ | 0.5 | 0.05 | 46.6 | M | 2.5 | 749 | toluene+ | 250 | 125 | 60 | 0 | 0.5 |
| 37 | II | C$_3$ | 0.5 | 0.28 | 10.0 | S | 2.1 | 529 | toluene+ | 250 | 125 | 60 | 0 | 0.5 |
| 38 | III | C$_3$ | 0.5 | 0.11 | 39.4 | M | 2.5 | 448 | toluene | 250 | 125 | 60 | 0 | 0.5 |
| 39 | III | C$_3$ | 0.5 | 0.56 | 8.0 | S | 3.0 | 527 | toluene+ | 250 | 125 | 60 | 0 | 0.5 |

(+ includes 0.2 ml of 25 wt % triisobutyl aluminum in heptane diluted in an additional 5 ml of toluene.)

TABLE 3

| Example # | P (g) | Activity* (kgP/mol · atm · hr) | TMC | MW | MWD | wt % | mol % | "r1" | Br | Vi1 | Tri | Vi2 | Vi3 |
|---|---|---|---|---|---|---|---|---|---|---|---|---|---|
| 4 | 4.7 | 826 | I | 77200 | 3.68 | — | — | — | 2.0 | 0.06 | 0.05 | 0.02 | 0.03 |
| 5 | 2.0 | 2578 | I | 336700 | 2.72 | — | — | — | 2.4 | 0.12 | 0.11 | 0.06 | 0.07 |
| 6 | 8.2 | 11697 | II | 690662 | 3.07 | — | — | — | 4.4 | 0.23 | 0.25 | 0.14 | 0.12 |
| 7 | 5.2 | 6871 | III | 385663 | 6.12 | — | — | — | 5.9 | 0.19 | 0.29 | 0.16 | 0.20 |
| 8 | 0.6 | 1904 | II | | | — | — | — | | | | | |
| 9 | 1.4 | 170 | I | 596884 | 5.77 | — | — | — | 3.1 | 0.16 | 0.11 | 0.08 | 0.16 |
| 10 | 2.5 | 1574 | II | 868179 | 2.22** | — | — | — | 4.3 | 0.76 | 0.42 | 0.25 | 0.14 |
| 11 | 1.1 | 233 | II | 516715 | 9.91** | — | — | — | 4.9 | 0.32 | 0.49 | 0.61 | 0.12 |
| 12 | 1.6 | 512 | III | | | — | — | — | 5.0 | 0.26 | 0.09 | 0.54 | 0.21 |
| 13 | 2.0 | 370 | III | | | — | — | — | 2.0 | 0.20 | 0.10 | 0.32 | 0.00 |
| 14 | 3.8 | 1288 | II | 542018 | 2.39** | — | — | — | 1.2 | 0.04 | 0.07 | 0.#9 | 0.04 |
| 15 | 1.0 | 159 | II | 142559 | 11.47** | — | — | — | 1.9 | 0.12 | 0.19 | 0.49 | 0.15 |
| 16 | 4.8 | 2030 | III | | | — | — | — | 0 | 0.05 | 0.05 | 0.03 | 0.04 |
| 17 | 2.1 | 315 | III | | | — | — | — | | 0.02 | 0.02 | 0.10 | 0.08 |
| 18 | 6.1 | 712 | III | 294129 | 3.51 | — | — | — | 1.0 | 0.07 | 0.00 | 0.13 | 0.09 |
| 19 | 1.4 | 75 | III | 107431 | 8.52** | — | — | — | 6.5 | 0.06 | 0.00 | 0.22 | 0.27 |
| 20 | 5.5 | 1789 | III | 238110 | 2.29 | 27.2 | 42.8 | 3.6 | 107.0 | 0.06 | 0.02 | 0.03 | 0.05 |
| 21 | 2.2 | 695 | II | | | 58.0 | 31.5 | 9.4 | 96.5 | 0.13 | 0.10 | 0.22 | 0.27 |
| 22 | 21.6 | 7025 | III | 241781 | 2.62 | 57.6 | 31.1 | 9.6 | 95.9 | 0.13 | 0.23 | 0.08 | 0.08 |
| 23 | 1.9 | 200 | II | | | 22.9 | 9.0 | 15.8 | 38.2 | 0.24 | 0.18 | 1.00 | 0.23 |
| 24 | 2.0 | 212 | II | | | 27.7 | 11.3 | 4.6 | 46.1 | 0.06 | 0.09 | 0.35 | 0.18 |
| 25 | 4.5 | 1298 | III | 462332 | 3.24** | 41.4 | 19.1 | 2.5 | 69.0 | 0.06 | 0.09 | 0.08 | 0.06 |
| 26 | 2.7 | 433 | III | 274061 | 7.62** | 38.5 | 17.2 | 2.9 | 64.1 | 0.02 | 0.06 | 0.15 | 0.04 |
| 27 | 3.3 | 513 | III | 240827 | 4.72** | 46.8 | 22.6 | 2.0 | 77.9 | 0.03 | 0.07 | 0.16 | 0.04 |
| 28 | 2.1 | 128 | II | | | 26.4 | 10.7 | 16.1 | 44.1 | 0.14 | 0.13 | 0.71 | 0.29 |
| 29 | 1.6 | 85 | II | | | 15.0 | 5.5 | 12.5 | 25.0 | 0.05 | 0.07 | 0.29 | 0.24 |
| 30 | 10.6 | 2127 | III | 275734 | 2.60 | 36.5 | 16.1 | 3.6 | 60.9 | 0.05 | 0.10 | 0.08 | 0.04 |
| 31 | 9.6 | 1054 | III | 235102 | 6.24 | 36.2 | 15.9 | 3.8 | 60.4 | 0.05 | 0.12 | 0.10 | 0.09 |
| 32 | 1.0 | 499 | II | 270,766 | 2.74 | — | — | — | — | 0.02 | 0.05 | 0.00 | 0.08 |
| 33 | 1.1 | 549 | II | 287,622 | 2.82 | — | — | — | — | 0.02 | 0.03 | 0.01 | 0.06 |
| 34 | 27.7 | 13,688 | III | 1,511,995 | 1.98 | — | — | — | — | 0.00 | 0.12 | 0.03 | 0.04 |
| 35 | 0.8 | 383 | I | 249,913 | 3.32** | — | — | — | — | 0.05 | 0.09 | 0.08 | 0.18 |
| 36 | 0.8 | 449 | II | | | — | — | — | — | 0.02 | 0.00 | 0.02 | 0.46 |
| 37 | 1.3 | 671 | II | 97,844 | 2.24** | — | — | — | — | | | | |

TABLE 3-continued

| Example # | P (g) | Activity* (kgP/mol · atm · hr) | TMC | MW | MWD | wt % | mol % | "r1" | Br | Vi1 | Tri | Vi2 | Vi3 |
|---|---|---|---|---|---|---|---|---|---|---|---|---|---|
| 38 | 9.7 | 3,481 | III | — | — | — | — | — | — | 0.03 | 0.05 | 0.06 | 0.07 |
| 39 | 28.5 | 10,008 | III | — | — | — | — | — | — | 0.02 | 0.04 | 0.01 | 0.04 |

*For $C_3$ polymerizations, kgP/mol · hr
**Mass balance of polymer from gpc lalls The GPC data for polymers of Examples 4–7, 9–11, 14–16, 18–20, 22, 25–27, 30–35 and 37 were examined for unimodality/multimodality. Polydispersities generally less than 3 were considered to be narrow. Examples 5, 10, 14, 16, 20, 22, 30 and 37 fall into this range and represent polymerizations by all three catalysts tested. Examples 4, 6, 7, 11 and 35 have polydispersities greater than 3.0 because of low molecular weight tails (species). Examples 9, 15, 18, 19, 25, 26, 27 and 31 are either bimodal or have broad shoulders, making their polydispersities greater than 3.0. The molecular weight distribution of Example 5 is seen in FIG. 1 and is typical of a unimodal, low polydisersity polymer. Polydispersities can be high in a semi-batch polymerization because of many reasons, including a too high reactor temperature exotherm, high comonomer conversion, presence of a scavenger, catalyst poisons in the reactor, or the like. Because of the formation of polymers with a narrow, unimodal molecular weight distribution in many of the examples, it is believed that symmetrically substituted tethered catalysts generally produce narrow polydispersity, unimodal polymers.

What is claimed is:

1. A tethered bidentate monocyclopentadienyl heteroatom compound activatable for use as an olefin polymerization catalyst, having the formula:

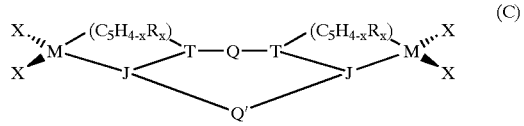

(C)

wherein

M is Ti, Zr or Hf;

each $C_5H_{4-x}R_x$ is independently a cyclopentadienyl ring substituted with from zero to four substituent groups R, x is a number from 0 to 4 denoting the degree of substitution, and each R is independently a radical selected from the group consisting of $C_1$–$C_{20}$ hydrocarbyl radicals, $C_1$–$C_{20}$ substituted hydrocarbyl radicals wherein one or more hydrogen atoms is replaced by a halogen atom, $C_1$–$C_{20}$ hydrocarbyl-substituted metalloid radicals wherein the metalloid is selected from the group consisting of Group 14 elements, and halogen radicals, or $C_5H_{4-x}R_x$ is a cyclopentadienyl ring in which two adjacent R-groups are joined to form a $C_4$–$C_{20}$ ring to give a saturated or unsaturated polycyclic cyclopentadienyl ligand;

each J is independently an element with a coordination number of 3 from Group 15;

each T is independently a covalent bridging group containing a Group 14 or 15 element;

each X is independently a univalent anionic ligand;

Q and Q' are independently divalent tethering group containing an element selected from the group consisting of Group 13, 14, 15 and 16 elements;

provided that:
(i) when Q is a hydrocarbylene diradical, each T independently comprises an alkyl or aryl silicon or germanium radical;
(ii) when Q is an oxygen diradical, each T is free of silicon; and
(iii) when Q contains silicon, germanium, nitrogen, or phosporus, T is free of carbon.

2. The compound of claim 1, wherein Q and Q' are independently a hydrocarbyl, halocarbyl, hydrohalocarbyl, silyl, disilyl, polysilyl, siloxy, disiloxy, polysiloxy, or disilylamide diradical, or a combination thereof.

3. The compound of claim 1, wherein Q and Q' are independently a hydrocarbyl, halocarbyl, or hydrohalocarbyl diradical.

4. The compound of claim 1, wherein each J is independently nitrogen or phosphorus.

5. The compound of claim 1, wherein each T is independently an alkyl or aryl silicon or germanium radical.

6. The compound of claim 1, wherein each T is independently an alkyl or aryl phosphine or amine radical, or a hydrocarbyl radical.

7. The compound of claim 1, comprising symmetrical metal centers.

* * * * *